US009437371B2

(12) United States Patent
Pena Hueso et al.

(10) Patent No.: US 9,437,371 B2
(45) Date of Patent: Sep. 6, 2016

(54) NITRILE-SUBSTITUTED SILANES AND ELECTROLYTE COMPOSITIONS AND ELECTROCHEMICAL DEVICES CONTAINING THEM

(71) Applicant: Silatronix, Inc., Madison, WI (US)

(72) Inventors: Jose Adrian Pena Hueso, Madison, WI (US); David Osmalov, Madison, WI (US); Jian Dong, Fort Collins, CO (US); Monica Usrey, Madison, WI (US); Michael Pollina, Elkridge, MD (US); Robert C. West, Madison, WI (US)

(73) Assignee: Silatronix, Inc., Madison, WI (US)

( * ) Notice: Subject to any disclaimer, the term of this patent is extended or adjusted under 35 U.S.C. 154(b) by 0 days.

(21) Appl. No.: 14/295,779

(22) Filed: Jun. 4, 2014

(65) Prior Publication Data

US 2014/0356735 A1    Dec. 4, 2014

Related U.S. Application Data

(60) Provisional application No. 61/830,851, filed on Jun. 4, 2013.

(51) Int. Cl.
| | |
|---|---|
| *H01M 10/0525* | (2010.01) |
| *H01G 11/58* | (2013.01) |
| *C07F 7/12* | (2006.01) |
| *H01M 10/0569* | (2010.01) |
| *H01G 11/60* | (2013.01) |
| *C07F 7/08* | (2006.01) |

(52) U.S. Cl.
CPC ............. *H01G 11/58* (2013.01); *C07F 7/0818* (2013.01); *C07F 7/12* (2013.01); *H01G 11/60* (2013.01); *H01M 10/0525* (2013.01); *H01M 10/0569* (2013.01); *H01M 2300/0028* (2013.01); *H01M 2300/0034* (2013.01); *Y02E 60/122* (2013.01); *Y02E 60/13* (2013.01)

(58) Field of Classification Search
None
See application file for complete search history.

(56) References Cited

U.S. PATENT DOCUMENTS

| | | | |
|---|---|---|---|
| 3,053,874 A * | 9/1962 | Pepe et al. | 556/415 |
| 4,730,073 A | 3/1988 | Takago et al. | |
| 2007/0065728 A1 | 3/2007 | Zhang et al. | |
| 2011/0266490 A1 | 11/2011 | West et al. | |
| 2012/0315536 A1* | 12/2012 | Bhat et al. | 429/199 |

FOREIGN PATENT DOCUMENTS

| | | |
|---|---|---|
| JP | 2000-243440 A | 9/2000 |
| JP | 2000243440 A * | 9/2000 |

OTHER PUBLICATIONS

Machine translation of JP 2000-342440 (Toriida).*

(Continued)

*Primary Examiner* — Barbara Gilliam
*Assistant Examiner* — Helen M McDermott
(74) *Attorney, Agent, or Firm* — Joseph T. Leone, Esq.; DeWitt Ross & Stevens S.C.

(57) ABSTRACT

Described herein are liquid, organosilicon compounds that including a substituent that is a cyano (—CN), cyanate (—OCN), isocyanate (—NCO), thiocyanate (—SCN) or isothiocyanate (—NCS). The organosilicon compounds are useful in electrolyte compositions and can be used in any electrochemical device where electrolytes are conventionally used.

10 Claims, 29 Drawing Sheets

(56) References Cited

OTHER PUBLICATIONS

PubChem. Compound Summary for: CID 14479. Create Date: Mar. 27, 2005. https://pubchem.ncbi.nlm.nih.gov/compound/14479.*
PubChem. Compound Summary for: CID 22079074. Create Date: Dec. 5, 2002. [retrieved on Nov. 6, 2014]. Retrieved from the Internet. <URL: https://pubchem.ncbi.nlm.nih.gov/compound/22079074?from=summary>. entire document.
PubChem. Compound Summary for: CID 57848168. Create Date: Aug. 19, 2012. [retrieved on Nov. 6, 2014]. Retrieved from the Internet. RL: https://pubchem.ncbi.nlm.nih.gov/compound/57848168?from=summary>. entire document.
PubChem. Compound Summary for: CID 4589186. Create Date: Sep. 16, 2005. [retrieved on Nov. 6, 2014]. Retrieved from the Internet. <URL: https://pubchem.ncbi.nlm.nih.gov/compound/4589186?from=summary>. entire document.

* cited by examiner

NITRILE-SUBSTITUTED SILANES AND ELECTROLYTE COMPOSITIONS AND ELECTROCHEMICAL DEVICES CONTAINING THEM

CROSS-REFERENCE TO RELATED APPLICATIONS

Priority is hereby claimed to provisional application Ser. No. 61/830,851, filed Jun. 4, 2013, which is incorporated herein by reference.

BACKGROUND

Liquid electrolytes in Li-ion batteries conventionally comprise a lithium salt, usually $LiPF_6$, in an organic solvent blend of ethylene carbonate (EC) and one or more co-solvents such as dimethyl carbonate (DMC), diethyl carbonate (DEC), or ethylmethyl carbonate (EMC). Unfortunately, $LiPF_6$ is unstable in these carbonate solvents above 60° C., as well as at charge voltages above 4.3 volts. Operation of a Li-ion battery above these temperatures or voltages results in rapid degradation of electrode materials and battery performance. In addition, current Li-ion electrolyte solvents exhibit flashpoints around 35° C., and are the major source of the energy released during an extreme Li-ion cell failure. Given these significant limitations, current electrolytes are impeding the development of advanced Li-ion batteries for all uses, including portable products, electric drive vehicles (EDVs), and utility scale use. A dramatic reduction in battery failure rate is also required for large scale Li-ion batteries to effectively serve applications in EDVs and grid storage.

Thus, there is a long-felt and unmet need for improved electrolyte solutions in energy storage devices such as Li-ion batteries.

SUMMARY OF THE INVENTION

Disclosed herein are organosilicon (OS) compounds for use as electrolyte solvents in electrochemical devices, among other uses.

In general, OS compounds are environmentally friendly, non-flammable, high temperature-resistant materials. These characteristics make OS materials well-suited for use as electrolyte solvents, binders, and coatings in energy storage devices. OS-based electrolytes are compatible with all lithium (Li) based electrochemical systems, including primary and rechargeable batteries, (i.e. Li-ion, Li-air), and capacitors (i.e. super/ultra-capacitors). The process of designing OS-based electrolytes into a Li battery involves limited changes in the cell design, and these electrolytes can be incorporated into production operations with existing manufacturing processes and equipment.

The OS compounds described herein can be used as liquid electrolyte solvents that replace the carbonate based solvent system in traditional Li-ion batteries. The OS-based solvents provide significant improvements in performance and abuse tolerance in Li-ion batteries, including increased thermal stability for longer life at elevated temperatures, increased electrolyte flash points for improved safety, increased voltage stability to allow use of high voltage cathode materials and achieve higher energy density, reduced battery failure rates for consistency with the requirements for large scale Li batteries used in EDV and grid storage applications, and compatibility with materials currently in use in Li-ion batteries for ease of adoption in current designs. Electrical double-layer capacitor (EDLC) devices have also demonstrated functionality with OS based electrolytes. The OS compounds described herein can be used in OS-based electrolyte blends to meet the requirements of specific applications in the industrial, military, and consumer product devices.

The objects and advantages of the compounds and electrolyte formulations will appear more fully from the following detailed description and accompanying drawings.

Disclosed herein are compounds of Formula I or Formula II:

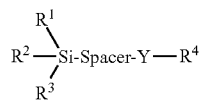

Formula I

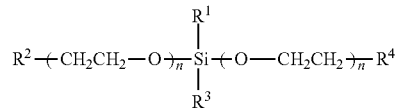

Formula II wherein $R^1$, $R^2$, and $R^3$ are the same or different and are independently selected from the group consisting of $C_1$ to $C_6$ linear or branched alkyl and halogen;

"Spacer" is absent or is selected from the group consisting of $C_1$ to $C_6$ linear or branched alkylene, alkenylene, or alkynylene, provided that when "Spacer" is absent, Y is present;

Y is absent or is selected from the group consisting of —$(O—CH_2—CH_2)_n$— and

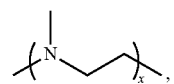

wherein each subscript "n" is the same or different and is an integer from 1 to 15, and subscript "x" is an integer from 1 to 15; and each $R^4$ is the same or different and is selected from the group consisting of cyano (—CN), cyanate (—OCN), isocyanate (—NCO), thiocyanate (—SCN) and isothiocyanate (—NCS).

Also specifically disclosed herein are compounds of Formula I, wherein "Spacer" is present, and Y is —$(O—CH_2—CH_2)_n$—. Additionally, specifically disclosed herein are compounds in which "Spacer" is present and Y is

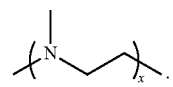

Additionally disclosed herein are compounds in which "Spacer" is absent, and Y is —$(O—CH_2—CH_2)_n$—.

Also disclosed herein are compounds having a structure as shown in any of Formulas II, III, IV, and V:

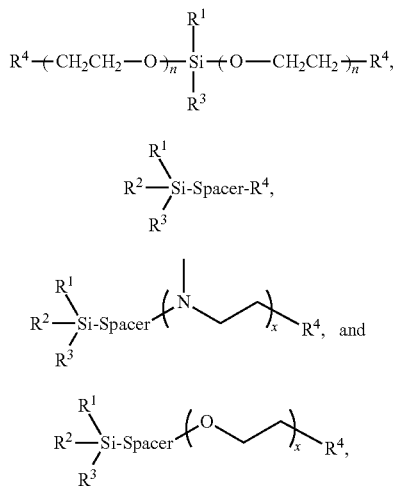

Formula II

Formula III

Formula IV

Formula V wherein $R^1$, $R^2$, and $R^3$ are the same or different and are independently selected from the group consisting of $C_1$ to $C_6$ linear or branched alkyl and halogen; "spacer" is a $C_1$ to $C_6$ linear or branched alkylene, alkenylene, or alkynylene; each $R^4$ is the same or different and is selected from the group consisting of cyano (—CN), cyanate (—OCN), isocyanate (—NCO), thiocyanate (—SCN) and isothiocyanate (—NCS); each subscript "n" is the same or different and is an integer from 1 to 15; "x" is an integer from 1 to 15. Also included herein are electrolyte compositions comprising one or more of the compounds of Formulas I, II, III, IV, V, as described herein, in combination with a salt, preferably a lithium-containing salt.

$R^1$, $R^2$, and $R^3$ may optionally be selected from the group consisting of $C_1$ to $C_3$ alkyl, chloro, and fluoro; and $R^4$ may optionally be cyano.

When the compound comprises Formula II, $R^1$ and $R^3$ may optionally be selected from the group consisting of $C_1$ to $C_3$ alkyl (or simply methyl), chloro, and fluoro. Each "n" is optionally and independently an integer from 1 to 5. $R^4$ may optionally be cyano.

When the compound comprises Formula III, $R^1$, $R^2$, and $R^3$ may optionally be selected from the group consisting of $C_1$ to $C_3$ alkyl, chloro, and fluoro. In some versions of the Formula II compounds at least one of $R^1$, $R^2$, and $R^3$ is halogen; in other versions of the Formula II compounds at least two of $R^1$, $R^2$, and $R^3$ are halogen. The "spacer" may optionally be a $C_2$ to $C_4$ linear or branched alkylene. $R^4$ may optionally be cyano.

When the compound comprises Formula IV, $R^1$, $R^2$, and $R^3$ may optionally be selected from the group consisting of $C_1$ to $C_3$ alkyl, chloro, and fluoro. In some versions of the Formula II compounds at least one of $R^1$, $R^2$, and $R^3$ is halogen; in other versions of the Formula II compounds at least two of $R^1$, $R^2$, and $R^3$ are halogen. The "spacer" may optionally be a $C_2$ to $C_4$ linear or branched alkylene. $R^4$ may optionally be cyano. In certain versions of the Formula II compounds, "x" may optionally be 1 to 4.

When the compound comprises Formula V, $R^1$, $R^2$, and $R^3$ may optionally be selected from the group consisting of $C_1$ to $C_3$ alkyl, chloro, and fluoro. In some versions of the Formula II compounds at least one of $R^1$, $R^2$, and $R^3$ is halogen; in other versions of the Formula II compounds at least two of $R^1$, $R^2$, and $R^3$ are halogen. The "spacer" may optionally be a $C_2$ to $C_4$ linear or branched alkylene. $R^4$ may optionally be cyano. In certain versions of the Formula II compounds, "x" may optionally be 1 to 4.

In all versions of the compounds, "halogen," includes fluoro, chloro, bromo, and iodo. Fluoro and chloro are the preferred halogen substituents. The term "lithium-containing salt" explicitly includes, but is not limited to, $LiClO_4$, $LiBF_4$, $LiAsF_6$, $LiPF_6$, $LiCF_3SO_3$, $Li(CF_3SO_2)_2N$, $Li(CF_3SO_2)_3C$, $LiN(SO_2C_2F_5)_2$, lithium alkyl fluorophosphates and lithium bis(chelato)borates.

Also disclosed herein are electrolyte compositions comprising one or more organosilicon compounds as recited in the preceding paragraphs. Also disclosed herein are electrochemical devices comprising such electrolyte compositions. The compounds disclosed herein are highly useful for formulating electrolytes for use in charge-storage devices of all kinds (e.g., cells, batteries, capacitors, and the like).

BRIEF DESCRIPTION OF THE DRAWINGS

FIG. 5A depicts a close-up of the same data shown in FIG. 5B.

FIG. 20A depicts a first cycle. FIG. 20B depicts a second cycle.

DETAILED DESCRIPTION OF THE INVENTION

Figure 1A:
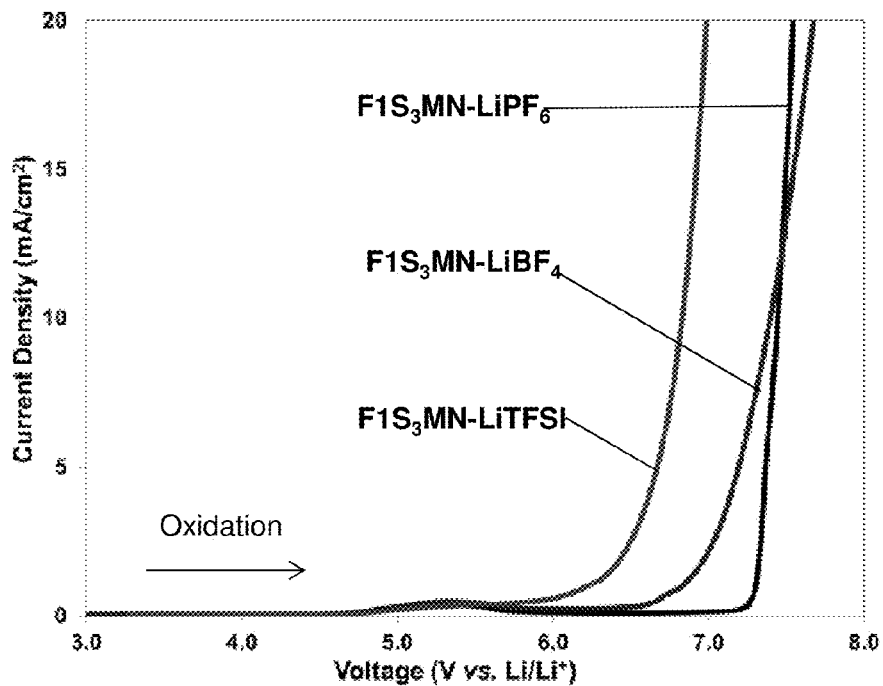
FIG. 1A depict the oxidation stability of $F1S_3MN$ with $LiPF_6$, $LiBF_4$, or LiTFSI in current density (mA/cm$^2$) versus voltage (V vs. Li/Li$^+$).

Throughout the description, a number of shorthand abbreviations will be used to designate various organo silicon compounds more easily. The following conventions are used:

The nNDnN compounds have the general formula:

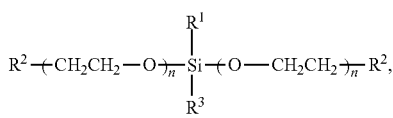

wherein R$^1$ and R$^3$ are the same or different and are independently selected from the group consisting of C$_1$ to C$_6$ alkyl, each R$^2$ is the same or different and is independently selected from the group consisting of cyano (—CN), cyanate (—OCN), isocyanate (—NCO), thiocyanate (—SCN) and isothiocyanate (—NCS), and the two subscripts "n" are integers that are the same or different and independently range from 1 to 15. Thus, for example, 1ND1N is the compound wherein R$^1$ and R$^3$ are methyl (i.e., C$_1$) and both subscripts "n" are 1.

The FnSnMN compounds have the general formula:

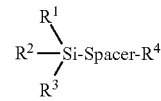

wherein R$^1$, R$^2$, and R$^3$ are the same or different and are independently selected from the group consisting of C$_1$ to C$_6$ alkyl (preferably methyl) and halogen (preferably F), "spacer" is a C1 to C6 linear or branched divalent hydrocarbon (i.e., alkylene, alkenylene, alkynylene), and R$^4$ is selected from the group consisting of cyano (—CN), cyanate (—OCN), isocyanate (—NCO), thiocyanate (—SCN) and isothiocyanate (—NCS). The compounds designated SnMN have the same structure, wherein R$^1$, R$^2$, and R$^3$ are the same or different and are independently selected from the group consisting of C$_1$ to C$_6$ alkyl (preferably methyl).

Related compounds disclosed herein have the structures:

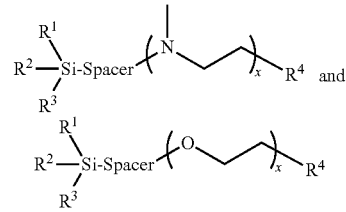

wherein R$^1$, R$^2$, and R$^3$ are the same or different and are independently selected from the group consisting of C$_1$ to C$_6$ alkyl (preferably methyl) and halogen (preferably F), "spacer" is a C1 to C6 linear or branched divalent hydrocarbon (i.e., alkylene, alkenylene, alkynylene), R$^4$ is selected from the group consisting of cyano (—CN), cyanate (—OCN), isocyanate (—NCO), thiocyanate (—SCN) and isothiocyanate (—NCS), and "x" is an integer of from 1 to 15, preferably from 1 to 4.

The compounds disclosed herein can be made by a number of different routes. A general approach that can be used to fabricate the compounds is as follows:

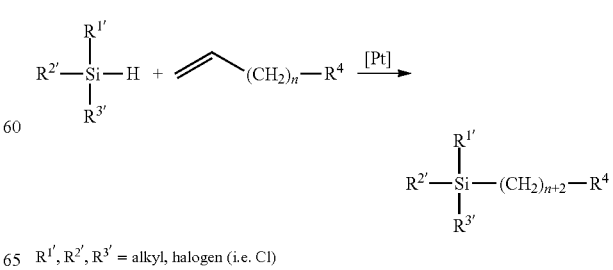

R$^{1'}$, R$^{2'}$, R$^{3'}$ = alkyl, halogen (i.e. Cl)

The various R groups are as defined herein; "n" is a positive integer.

The compounds disclosed herein can also be fabricated via the following approach:

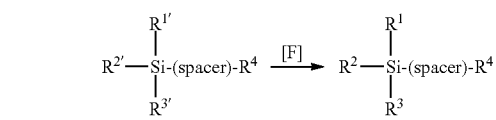

$R^{1'}, R^{2'}, R^{3'}$ = alkyl, chloride $R^1, R^2, R^3$ = alkyl, fluoride

The compounds disclosed herein are also made by a number of specific routes, including the following reaction schemes:

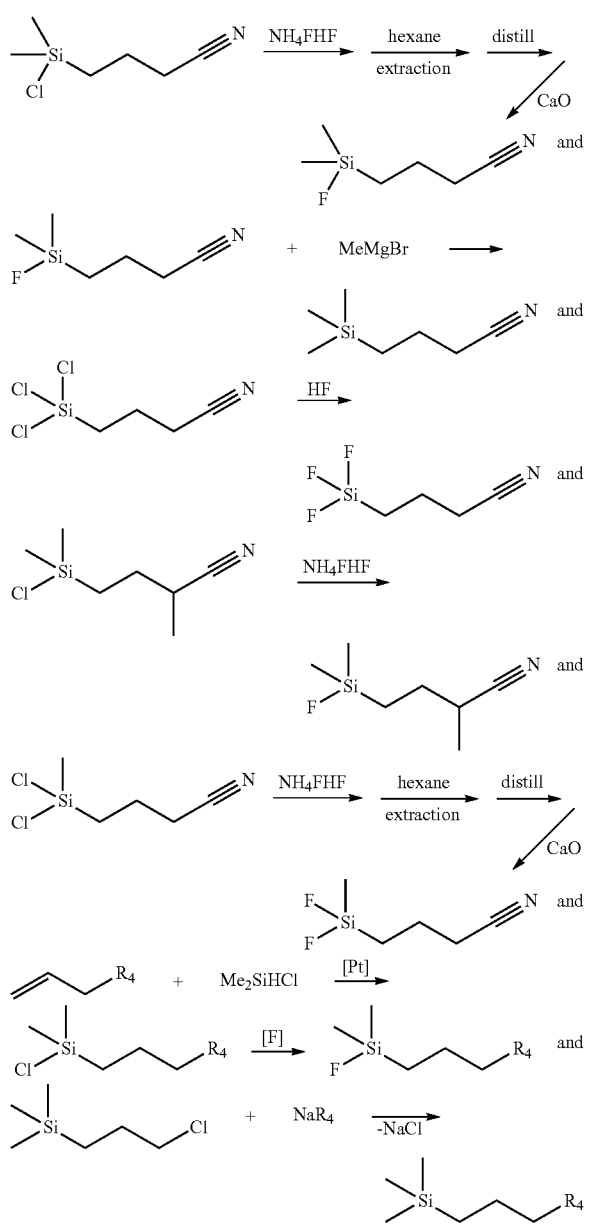

($R^4$ as defined above) and

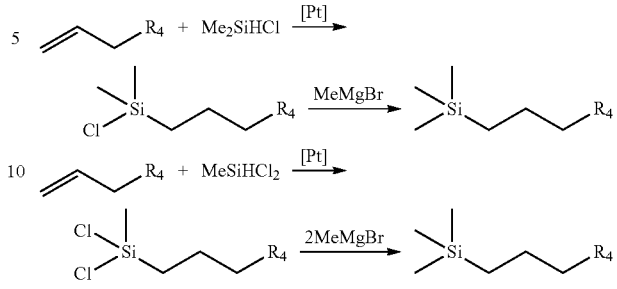

LiTFSI is a commercial product supplied by several international suppliers:

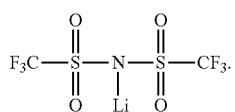

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the compounds and compositions disclosed herein are not confined to the particular construction and arrangement of parts herein illustrated and described, but embraces such modified forms thereof as come within the scope of the claims.

The presently disclosed compounds are organosilicon compounds having a shared structural feature in the form of a one or more terminal substituents that comprise a carbon-nitrogen double or triple bond, such as a cyano (R—C≡N), cyanate (R—O—C≡N), isocyanate (R—N=C=O), thiocyanate (R—S—C≡N), and/or isothiocyanate (R—N=C=S). Included among the preferred compounds are the following structures:

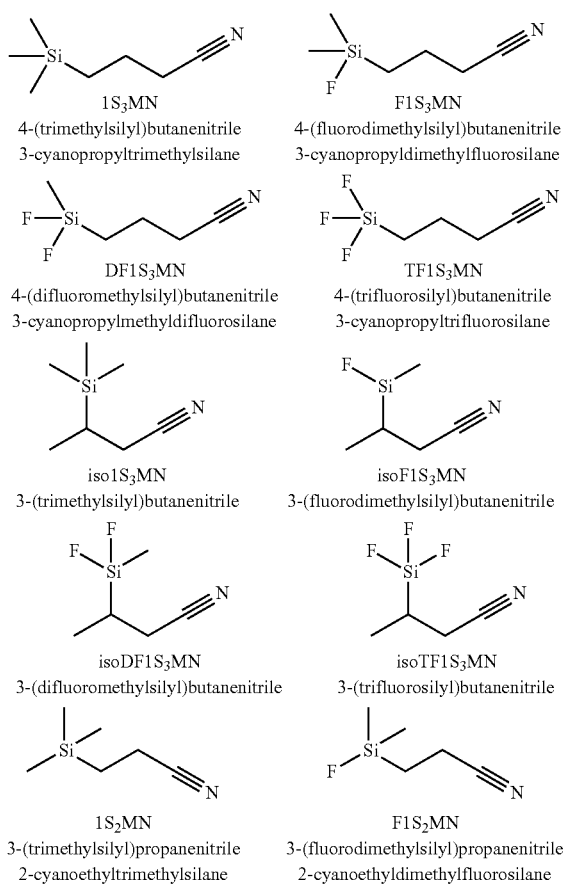
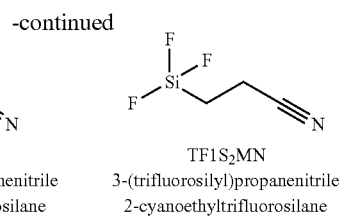

The above structures are all depicted with a terminal cyano group. This is for purposes of brevity only. The analogous compounds having a terminal cyanate, isocyanate, or thiocyanate moiety in place of the cyano moiety are explicitly within the scope of the disclosure. Likewise, the halogenated compounds are depicted above as fluorinated compounds. The analogous compounds having other halogen substituents (chlorine, bromine, and/or iodine) in place of fluorine atoms are explicitly within the scope of the present disclosure. For each compound listed, two alternative systematic names are provided (the first of each pair of names designates the fundamental core as a nitrile; the second designated the fundamental cores as silane.) Additionally, each compound has been given a short-hand designation in which DF=difluoro, TF=trifluoro, and "Sn" designates the alkylene spacer between the silicon atom and the terminal cyanate, isocyanate, or thiocyanate moiety and "n" represents the number of carbon atoms in the spacer. The physical properties of selected organosilicon (OS) compounds are presented in Table 1.

As shown in Table 1, Reduced viscosity, higher conductivity, and lower flash point with added fluorine and reduced spacer length. DF1S$_2$MN has lowest viscosity and highest conductivity.

TABLE 1

| | Physical Properties (with 20% EC, additives, 1M LiPF$_6$) | | | | | | |
|---|---|---|---|---|---|---|---|
| | Properties of Neat Solvent | | | | Properties of Electrolytes with 1M LiPF$_6$ | | |
| Solvent | MW (g/mol) | Flash Point (° C.) | Dielectric Constant (neat) | B.P. (° C.) | Co-solvent | 30° C. Conductivity (mS/cm) | 30° C. Viscosity (cP) | Flash Point (° C.) |
| 1S$_3$MN | 141 | 72 | 12.6 | 200 | Not compatible with EC | | | |
| F1S$_3$MN | 145 | 82 | 16.8 | 249 | 20% EC | 3.5 | 9.1 | 82 |
| F1S$_3$cMN | 159 | 80 | 16.6 | n/a | 20% EC | 2.6 | 10.6 | n/a |
| DF1S$_3$MN | 149 | 78 | 18.2 | 202 | 20% EC | 4.8 | 8.2 | 78 |
| DF1S$_2$MN | 135 | 64 | 19.5 | 182 | 20% EC | 5.8 | 6.9 | 64 |
| F1S$_3$M2 | 238 | 112 | 7.2 | 233 | 20% EC | 3.0 | 14.0 | 112 |

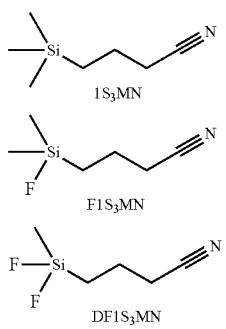

TABLE 1-continued

Physical Properties (with 20% EC, additives, 1M LiPF$_6$)

| Solvent | Properties of Neat Solvent | | | | Properties of Electrolytes with 1M LiPF$_6$ | | | |
|---|---|---|---|---|---|---|---|---|
| | MW (g/mol) | Flash Point (° C.) | Di-electric Constant (neat) | B.P. (° C.) | Co-solvent | 30° C. Conductivity (mS/cm) | 30° C. Viscosity (cP) | Flash Point (° C.) |

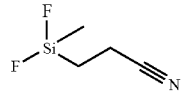

DF1S$_2$MN

F1S$_3$M2

F1S$_3$cMN

The physical properties of neat 1ND2, 1ND1, 1ND1N and F1S$_3$MN, as well as electrolyte solutions containing these solvents, are shown in Table 2:

TABLE 2

Physical Properties of Solvents and Electrolytes

| | Properties of Neat Solvent | | | | Properties of Electrolytes with 1 M Salt | | | |
|---|---|---|---|---|---|---|---|---|
| Solvent | RT Visc. (cP) | Flash Point (° C.) | Di-electric Constant (neat) | B.P. (° C.) | Batch, Co-solvent, Salt | 30° C. Conductivity (mS/cm) | 30° C. Viscosity (cP) | Flash Point (° C.) |
| 1ND1N | 8.3 | 168 | 30 | n/a | ZP791 20% EC LiPF$_6$ | 1.9 | 33 | 80 |
| | | | | | ZP779 ZP780 LiPF$_6$ | 1.3 | 29 | 72 |
| | | | | | ZT778 LiTFSI | 1.1 | 37 | 166 |
| 1ND1 | n/a | 85 | 8.1 | n/a | CP630 20% EC LiPF$_6$ | 4.5 | 5.1 | 52 |
| 1ND2 | 3.5 | 138 | 6.4 | 288 | CP597 20% EC LiPF6 | 3.9 | 12.5 | 130 |
| F1S$_3$MN | 2.0 | 82 | 16.8 | 249 | ZP82$_6$ 20% EC LiPF$_6$ | 3.5 | 9.1 | 82 |
| | | | | | ZP825 LiPF$_6$ | 2.7 | 8.3 | 58 |

In addition to the organosilicon compounds disclosed herein, the present electrolyte compositions may include conventional non-silicon co-solvents. For example, the present electrolyte compositions may include nitriles and carbonates, such as acetonitrile, ethylene carbonate (EC), dimethyl carbonate (DMC), diethyl carbonate (DEC), or ethylmethyl carbonate (EMC). The instant electrolyte compositions may include non-silicon co-solvents at a wide range of concentrations, including but not limited to, about 1 wt % to about 40 wt %. Examples of suitable co-solvent concentrations include about 1 wt %, about 5 wt %, about 10 wt %, about 15 wt %, about 20 wt %, about 25 wt %, about 30 wt %, about 40 wt % or a range between and including any of the preceding amounts.

EXAMPLES

F1S$_3$MN Synthesis:

Scheme 1 depicts a synthesis scheme for F1S$_3$MN. [F] indicates a fluorinating agent, such as HF, NH$_4$FHF, or other fluorinating agent. NH$_4$FHF is preferably used as a fluorinating agent for laboratory scale synthesis. If HF is used, the only byproduct is HCl. The synthesized F1S$_3$MN compound is washed from the solid salt with hexane, distilled, dried with CaO, and distilled again.

Scheme 1

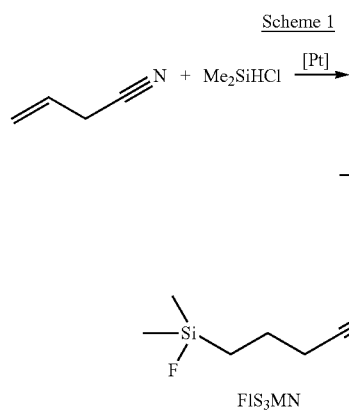

Scheme 2 depicts a synthesis scheme for F1S₃MN using NH₄FHF as a fluorinating agent. Using Karstedt's catalyst (Platinum(0)-1,3-divinyl-1,1,3,3-tetramethyldisiloxane complex solution, Cat. No. 479519, Sigma-Aldrich, St. Louis, Mo.), about 3% substitution on the secondary carbon occurs, generating isoF1S₃MN. The isoF1S₃MN has a lower boiling point than F1S₃MN, and most of it can be separated by fractional distillation.

Scheme 2

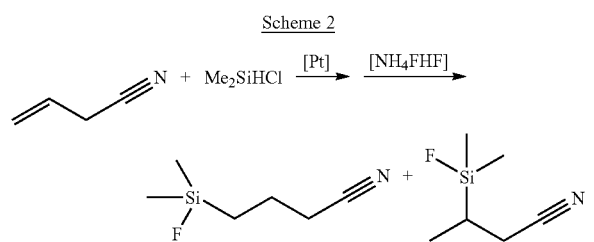

Scheme 3 depicts an alternative, shorter synthesis scheme for F1S₃MN using a ClS₃MN intermediate. The ClS₃MN intermediate can be obtained by Gelest, Inc. (Product Code SIC2452.0, 11 East Steel Road, Morrisville, Pa.). Use of the ClS₃MN intermediate reduces the time spent during synthesis.

Scheme 3

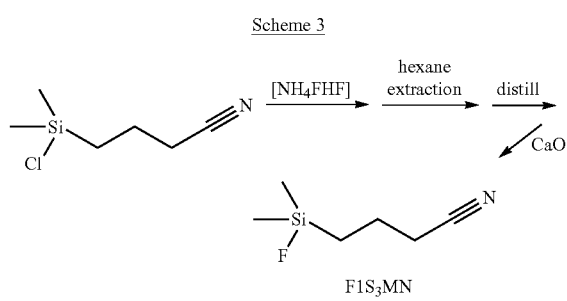

Scheme 4 depicts yet another synthesis scheme for F1S₃MN. As with Scheme 1, [F] indicates a fluorinating agent, such as HF, NH₄FHF, or other fluorinating agent. The use of HF as fluorinating agent in this synthesis scheme will not give solid byproducts, so there is no need of hexane extraction and filtration of solid. The only byproduct is HCl.

Scheme 4

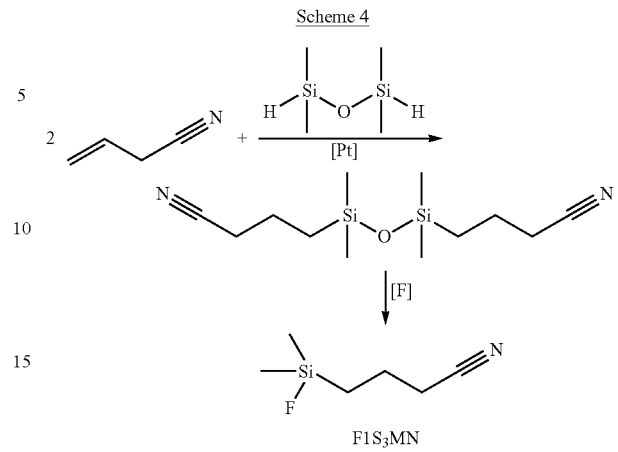

Scheme 5 depicts yet another synthesis scheme for F1S₃MN. As with Scheme 1, [F] indicates a fluorinating agent, such as HF, NH₄FHF, or other fluorinating agent.

Scheme 5

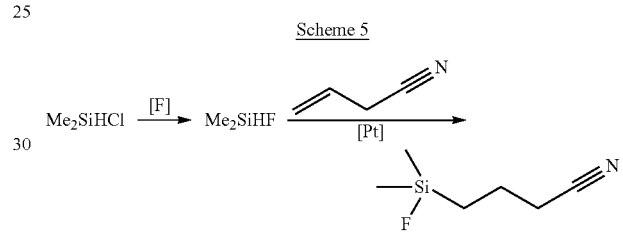

Synthesis of F1S₃MN:

In the preferred route, allyl cyanide is heated to about 100° C. with a small amount of Karstedt's catalyst. Dimethylchlorosilane was added dropwise and refluxed 4 hours. After cooling to room temperature, the mixture was fluorinated using 1 mol equivalent of ammonium hydrogen fluoride at room temperature. Cold hexane was added to the mixture, the solid was filtered off, and the solvent evaporated. Calcium oxide was added to the crude product and it was distilled under vacuum between 45-55° C. at 0.4 Torr to yield the desired product, F1S₃MN.

Determination of the Electrochemical Stability of Organosilicon Materials:

Computational chemistry methods were used to calculate electrochemical properties of various organosilicon molecules. We used the GAMESS program developed by the Gordon research group at Iowa State University for the Density Function Theory (DFT) molecular orbital calculations. The HOMO (highest occupied molecular orbital) and LUMO (lowest unoccupied molecular orbital) energy levels, which correlate to the reduction and oxidation potentials of compounds, were calculated at the B3LYP/DZV level.

The oxidative stability of electrolytes containing organosilicon solvents was determined using linear sweep voltammetry (LSV) or cyclic voltammetry (CV) in a 3-electrode cell. A platinum microelectrode was used as the working electrode with lithium metal as both the counter and reference electrode. The potential of the system was increased from the open circuit voltage (OCV) to 6 or 8V (vs. Li/Li+) at a scan rate of 10 mV/s. The resulting current density (mA/cm2) was recorded at each potential with a higher current indicating an oxidative reaction (i.e., lower oxidative stability). For the linear sweep voltammetry, 8V was used as a final potential to evaluate the fundamental oxidative stability of the material across a wider voltage range. For the cyclic voltammetry, 6V was used to evaluate the material across multiple scans under potentials more relevant to traditional battery applications. Multiple scans were conducted in the cyclic voltammetry experiments to determine the reversibility/irreversibility of any reactions observed.

The reductive stability of electrolytes containing organosilicon solvents was determined using linear sweep voltammetry (LSV) in a 3-electrode cell. A glassy carbon electrode was used as the working electrode with lithium metal as both the counter and reference electrode. The potential of the system was decreased from the open circuit voltage (OCV, typically 3V) to 0.1V (vs. Li/Li+) at a scan rate of 10 mV/s. The resulting current density ($mA/cm^2$) was recorded at each potential with a greater current indicating a reduction reaction (i.e., lower reductive stability). Two scans were conducted to evaluate if the reductive processes were reversible or irreversible (i.e., passivating).

Electrochemical Stability of $F1S_3MN$:

Molecular orbital diagrams for $F1S_3MN$ and $F1S_3M2$, not shown, reveal that the energy difference between the highest occupied molecular orbital (HOMO) and the lowest unoccupied molecular orbital (LUMO) is greater for $F1S_3MN$ (9.07 eV) than for $F1S_3M2$ (8.20 eV). $F1S_3MN$ also has a higher oxidation potential (−8.75 eV) than $F1S_3M2$ (−6.84 eV).

Figure 1B:
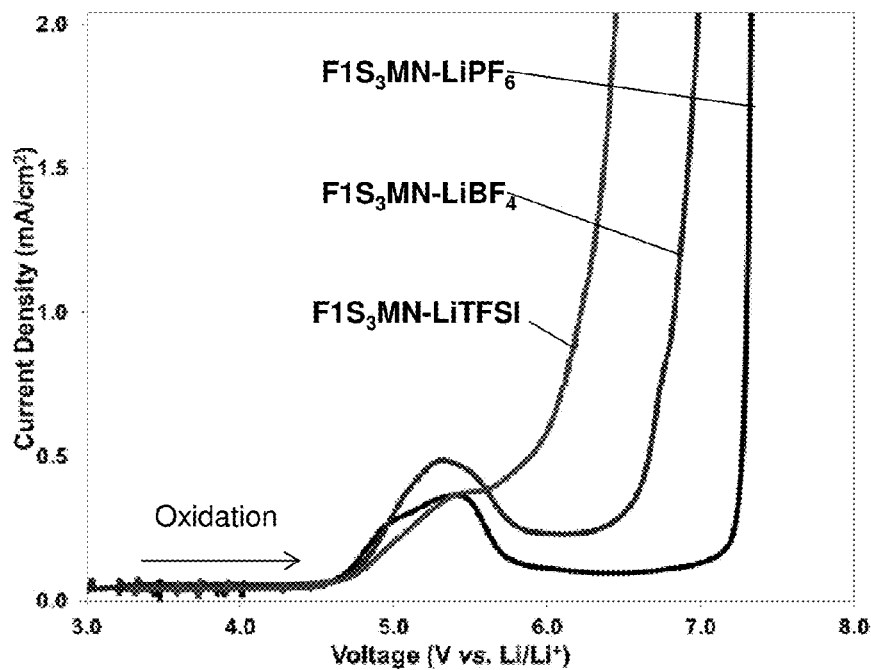
FIG. 1B depicts a close-up of the same data shown in FIG. 1A.

FIGS. 1A and 1B depict the oxidation stability of $F1S_3MN$ with $LiPF_6$, $LiBF_4$, or LiTFSI in current density ($mA/cm^2$) versus voltage (V vs. $Li/Li^+$). The oxidation stability was tested at room temperature with a working electrode as Pt, a counter electrode as Li, a reference electrode as $Li/Li^+$, and a sweep rate of 10 mV/s. FIG. 1B depicts a close-up of the same data shown in FIG. 1A. The $F1S_3MN$-$LiPF_6$ electrolyte exhibited the best oxidation stability, having a current density of 1 $mA/cm^2$ at 7.3 V compared to a current density of 1 $mA/cm^2$ at 6.8 V and 6.2 V for $F1S_3MN$-$LiBF_4$ and $F1S_3MN$-LiTFSI, respectively.

Figure 2A:
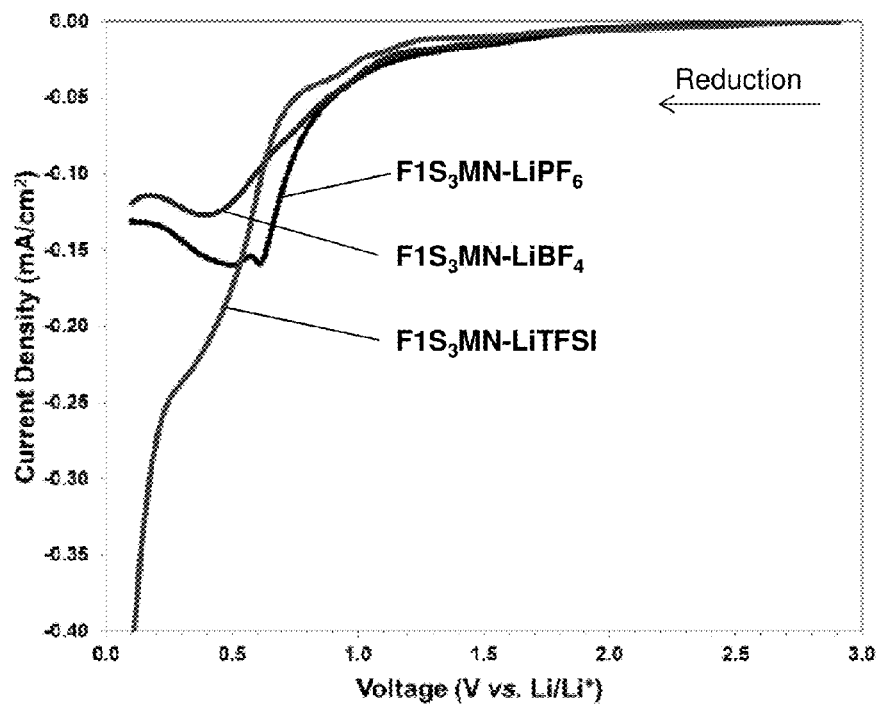
FIG. 2A and FIG. 2B depict duplicate runs to measure the reduction stability of $F1S_3MN$ with $LiPF_6$, $LiBF_4$, or LiTFSI in current density (mA/cm$^2$) versus voltage (V vs. Li/Li$^+$).
Figure 2B:
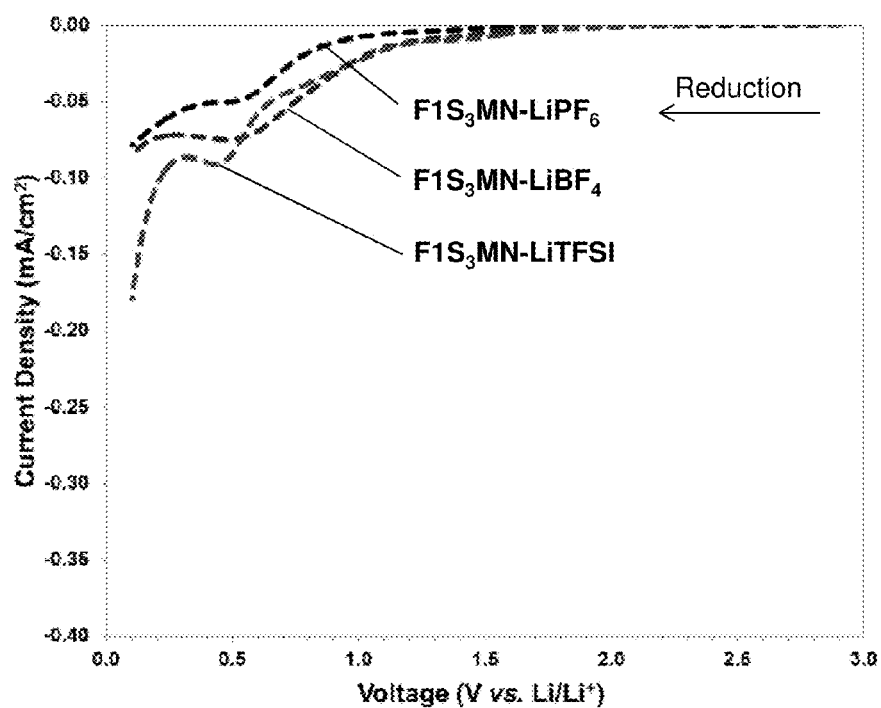

FIGS. 2A and 2B depict the reduction stability of $F1S_3MN$ with $LiPF_6$, $LiBF_4$, or LiTFSI in current density ($mA/cm^2$) versus voltage (V vs. $Li/Li^+$). The reduction stability was tested at room temperature with a working electrode as Pt, a counter electrode as Li, a reference electrode as $Li/Li^+$, and a sweep rate of 10 mV/s. FIGS. 2A and 2B are two separate scans. The $F1S_3MN$-$LiPF_6$ electrolyte exhibited the best reduction stability.

Figure 3A:
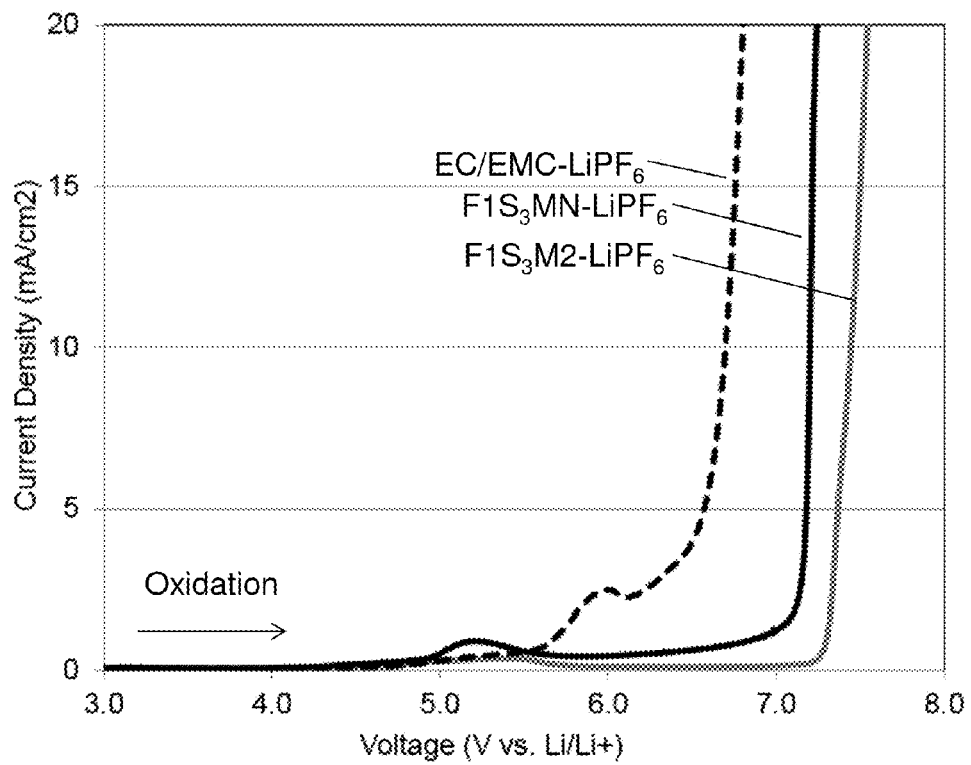
FIG. 3A depicts the oxidation stability of $F1S_3MN$ or $F1S_3M2$ with 1M $LiPF_6$ in current density (mA/cm$^2$) versus voltage (V vs. Li/Li$^+$).
Figure 3B:
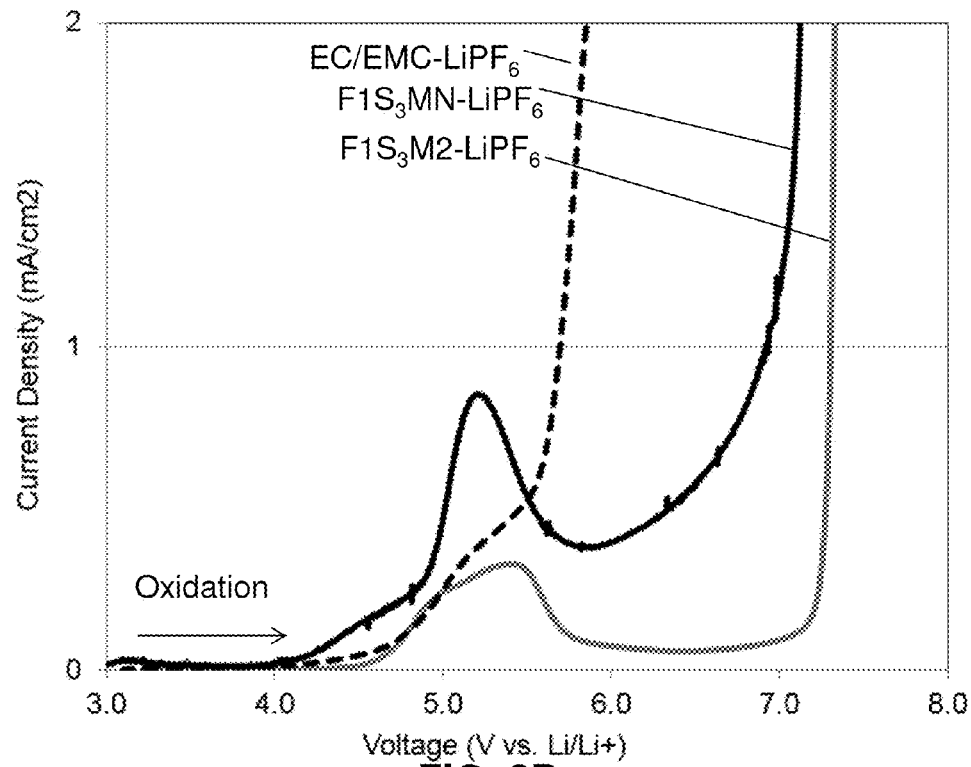
FIG. 3B depicts a close-up of the same data shown in FIG. 3A.

FIGS. 3A and 3B depict the oxidation stability of $F1S_3MN$ or $F1S_3M2$ with 1M $LiPF_6$ in current density ($mA/cm^2$) versus voltage (V vs. $Li/Li^+$). The oxidation stability was tested at room temperature with a working electrode as Pt, a counter electrode as Li, a reference electrode as $Li/Li^+$, and a sweep rate of 10 mV/s. FIG. 3B depicts a close-up of the same data shown in FIG. 3A. $F1S_3MN$ demonstrated improved oxidation stability with respect to $F1S_3M2$.

Figure 4:
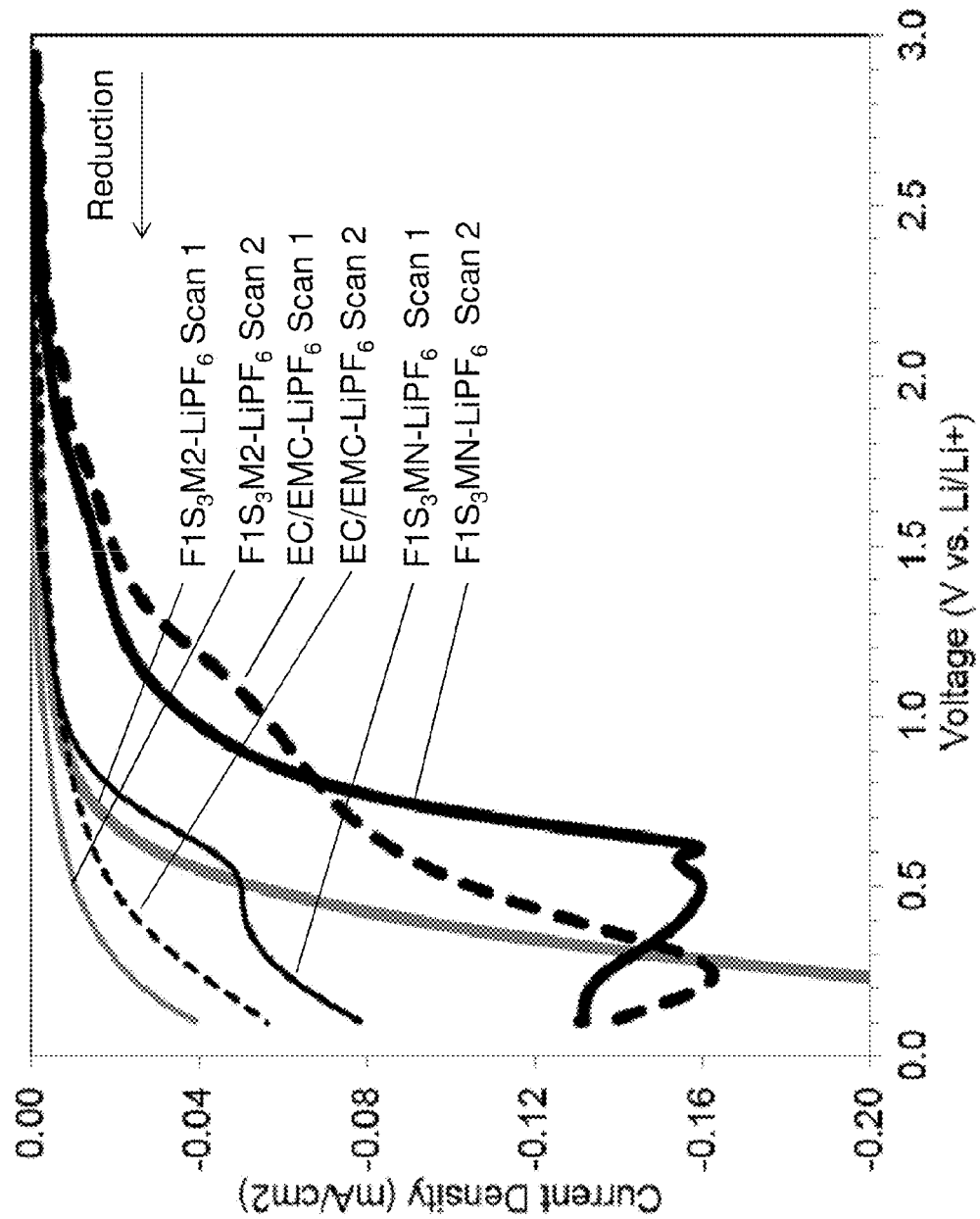
FIG. 4 depicts the reduction stability of $F1S_3MN$ or $F1S_3M2$ with 1M $LiPF_6$ in current density (mA/cm$^2$) versus voltage (V vs. Li/Li$^+$).

FIG. 4 depicts the reduction stability of $F1S_3MN$ or $F1S_3M2$ with 1M $LiPF_6$ compared to a carbonate control electrolyte with $LiPF_6$ in current density ($mA/cm^2$) versus voltage (V vs. $Li/Li^+$) in two separate scans. The reduction stability was tested at room temperature with a working electrode as Pt, a counter electrode as Li, a reference electrode as $Li/Li^+$, and a sweep rate of 10 mV/s. $F1S_3MN$ demonstrated less resistance to reduction compared to $F1S_3M2$.

Determination of Thermal Stability of Neat Solvents & Formulated Electrolytes:

The thermal stability of both the neat organosilicon solvents and the electrolyte compositions were determined as follows: Approximately 0.75 mL of liquid sample was heated in a sealed cell under an argon purge. The Argon purge was carried to an atmospheric sampling mass spectrometer where any gas phase impurities and/or decomposition products can be detected at very low levels using electron impact mass spectrometry (EI-MS). The sample was held for 1 hour at pre-determined temperature levels that are relevant for battery applications (30, 55, 70, 100, 125, 150, 175, and 200° C.). The gas phase decomposition products were identified by comparing fragmentation patterns obtained from the EI-MS to NIST standards. Following the heating experiment (and detection/collection of all gas phase products), the remaining liquid sample was analyzed via NMR spectroscopy for a quantitative analysis of the extent of decomposition. Multiple nuclei were examined to fully analyze all components of the system, including the organosilicon solvent, any carbonate co-solvents, all additives, and the lithium salt (if present).

Figure 5A:
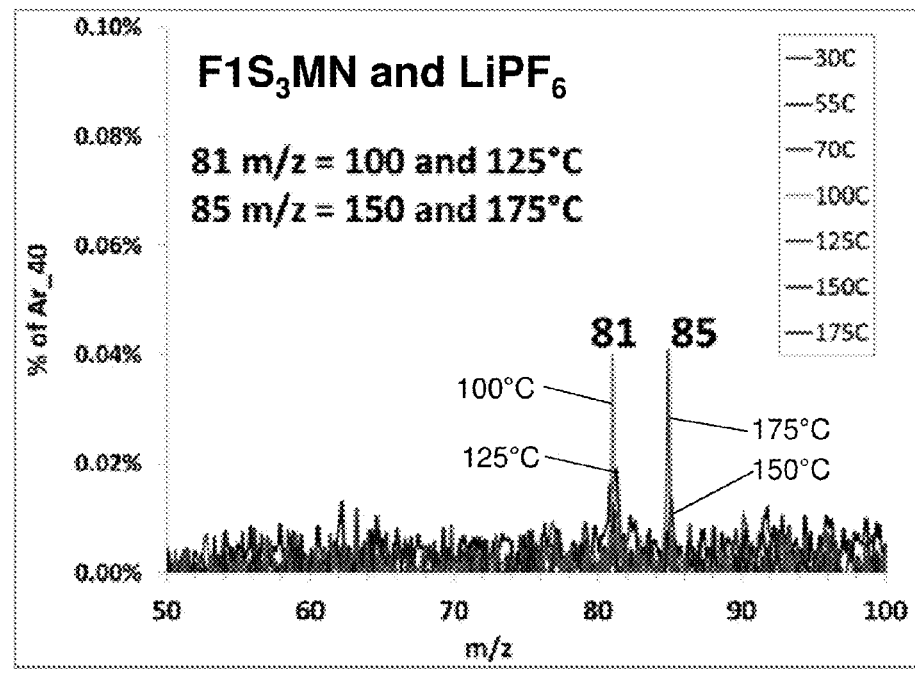
FIGS. 5A and 5B depict the thermal stability of $F1S_3MN$ with $LiPF_6$.
Figure 5B:
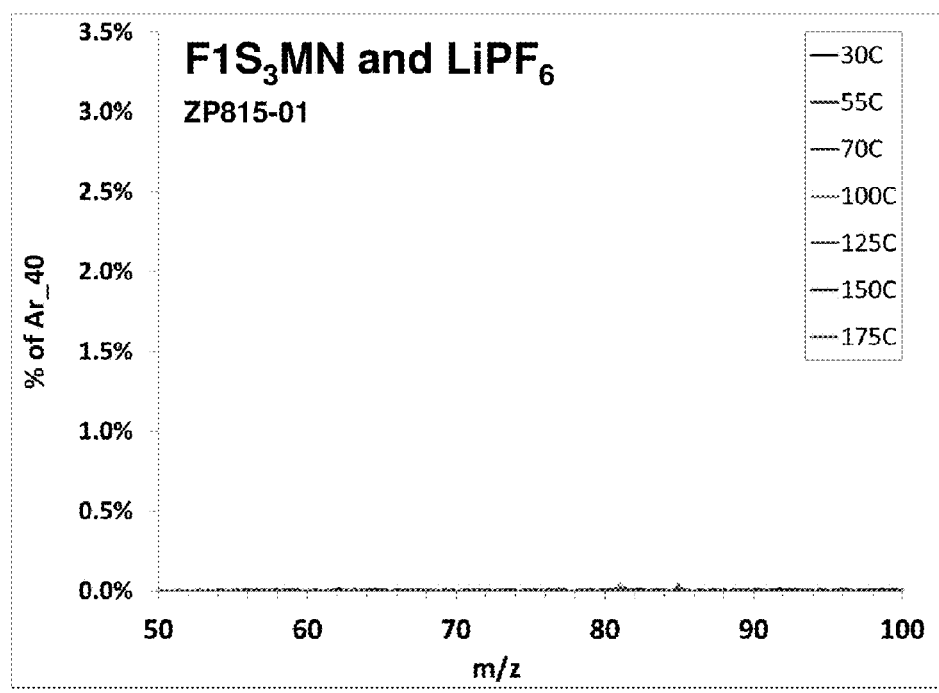

Thermal Stability of $F1S_3MN$:

FIGS. 5A and 5B depict the thermal stability of $F1S_3MN$ with $LiPF_6$. $F1S_3MN$-$LiPF_6$ electrolyte (batch ZP815-01) was exposed to temperatures ranging from 30° C. to 175° C. and analyzed by electron impact mass spectrometry (EI-MS) and nuclear magnetic resonance spectroscopy (NMR) for gas and liquid decomposition products, respectively. The temperatures at which salient peaks appeared are annotated. $F1S_3MN$ showed no significant gas and/or liquid phase decomposition up to 175° C. $Me_2SiF_2$ appeared at temperatures of 100-125° C. at 81 m/z, and $MeSiF_3$ appeared at temperatures of 150-175° C. at 85 m/z. However, the 81 m/z and 85 m/z peaks appeared inconsistently at 100-175° C. Furthermore, $^1H$ NMR analysis showed no decomposition after heating to 175° C. Therefore, $F1S_3MN$ does not show consistent decomposition up to 175° C. FIG. 5A depicts a close-up of the same data shown in FIG. 5B.

Figure 6:
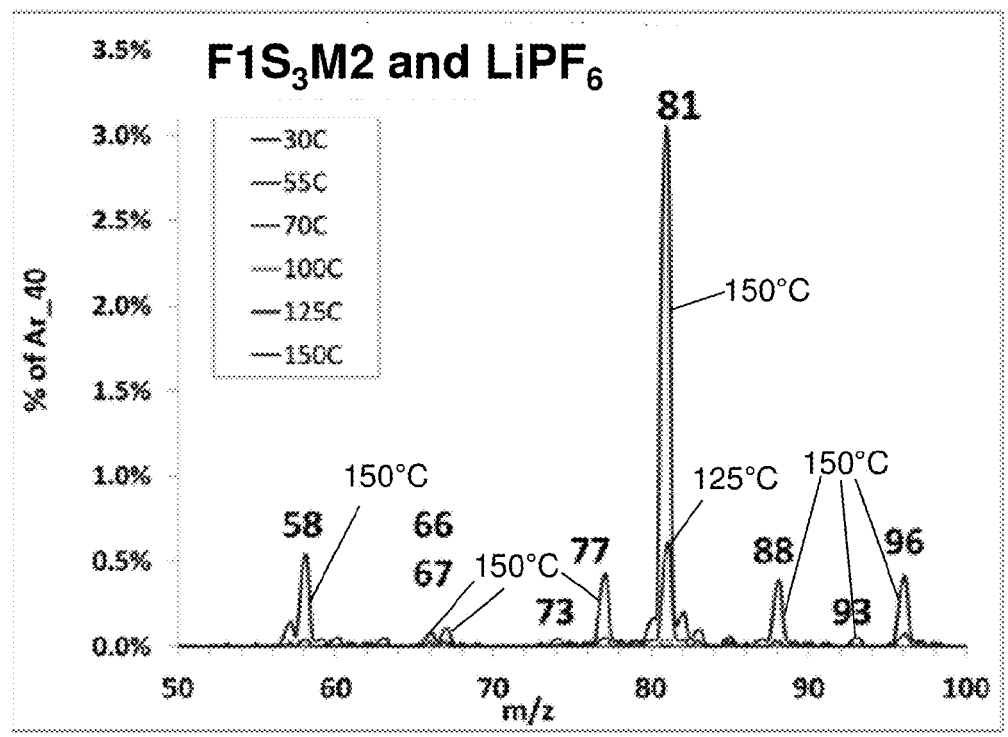
FIG. 6 depicts the thermal stability of $F1S_3M2$ with $LiPF_6$.

FIG. 6 depicts the thermal stability of $F1S_3M2$ with $LiPF_6$. $F1S_3M2$-$LiPF_6$ electrolyte was exposed to temperatures ranging from 30° C. to 150° C. and analyzed by mass spectrometry for decomposition products. The temperatures at which salient peaks appeared are annotated. $F1S_3M2$ showed decomposition at temperatures ≥125° C. Decomposition products included $Me_2SiF_2$ and 1,4-dioxane. $^1H$ NMR analysis showed approximately 6% decomposition at 150° C. These results in combination with those discussed in relation to FIG. 5A and FIG. 5B indicate that $F1S_3MN$ is more thermally stable than $F1S_3M2$.

Figure 7:
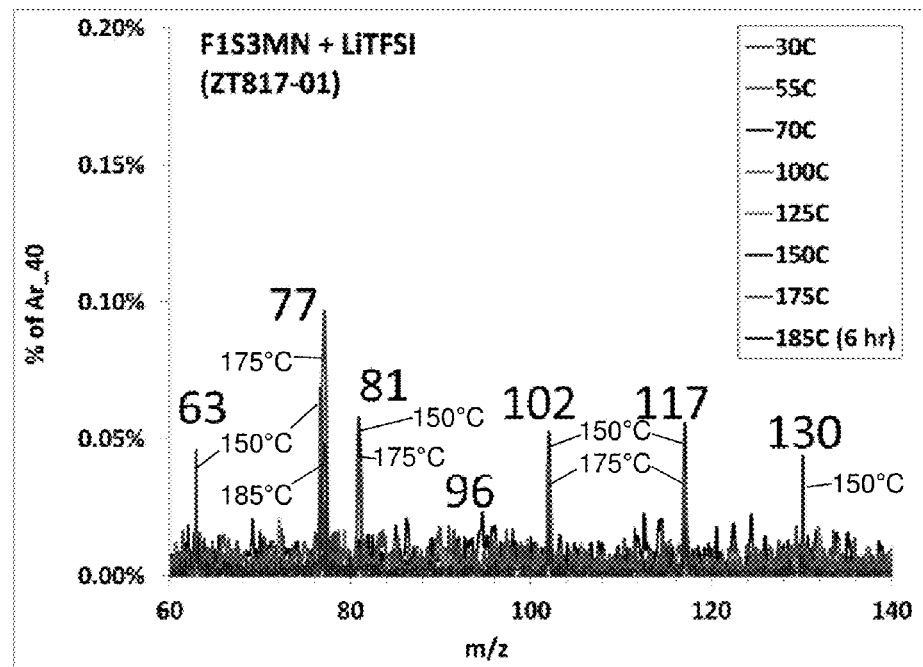
FIG. 7 depicts the thermal stability of $F1S_3MN$ with LiTFSI.

FIG. 7 depicts the thermal stability of $F1S_3MN$ with LiTFSI. $F1S_3MN$-LiTFSI electrolyte was exposed to temperatures ranging from 30° C. to 185° C. and analyzed by mass spectrometry for decomposition products. The temperatures at which salient peaks appeared are annotated. Gas phase peaks were observed at temperatures ≥150° C. Peaks at 117 and 102 matched patterns observed for $F1S_3MN$-$LiBF_4$ electrolyte and neat solvent (see FIGS. 8 and 9).

Figure 8:
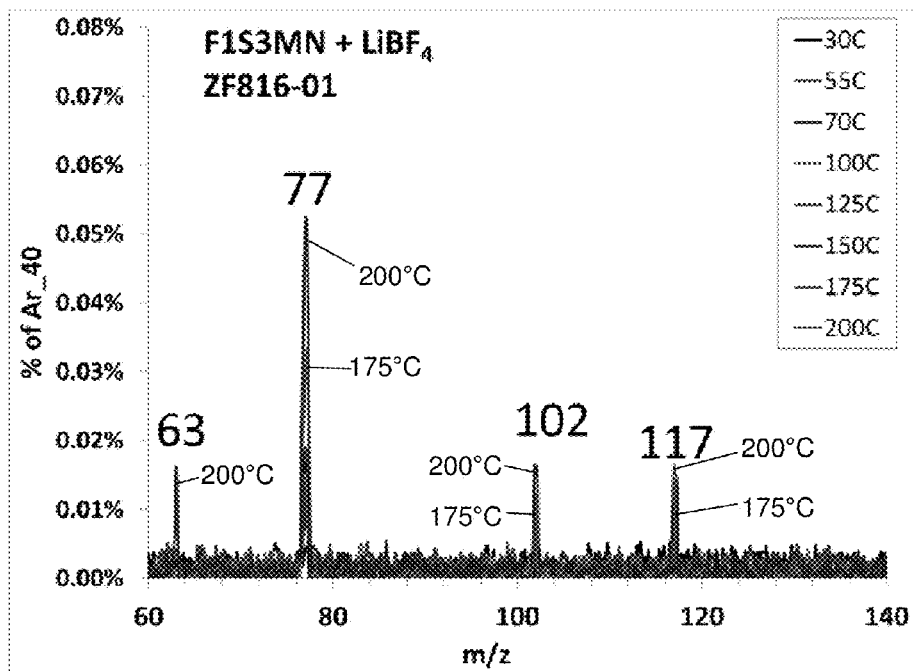
FIG. 8 depicts the thermal stability of $F1S_3MN$ with $LiBF_4$.

FIG. 8 depicts the thermal stability of $F1S_3MN$ with $LiBF_4$. $F1S_3MN$-$LiBF_4$ electrolyte was exposed to temperatures ranging from 30° C. to 200° C. and analyzed by mass spectrometry for decomposition products. The temperatures at which salient peaks appeared are annotated. Gas phase peaks were observed at temperatures ≥175° C. Peaks at 117 and 102 matched patterns observed for neat solvent and $F1S_3MN$-LiTFSI electrolyte (see FIGS. 7 and 9). $^1H$ NMR analysis showed no fluorinated decomposition products and <0.5% of a non-fluorinated hydrolysis product.

Figure 9:
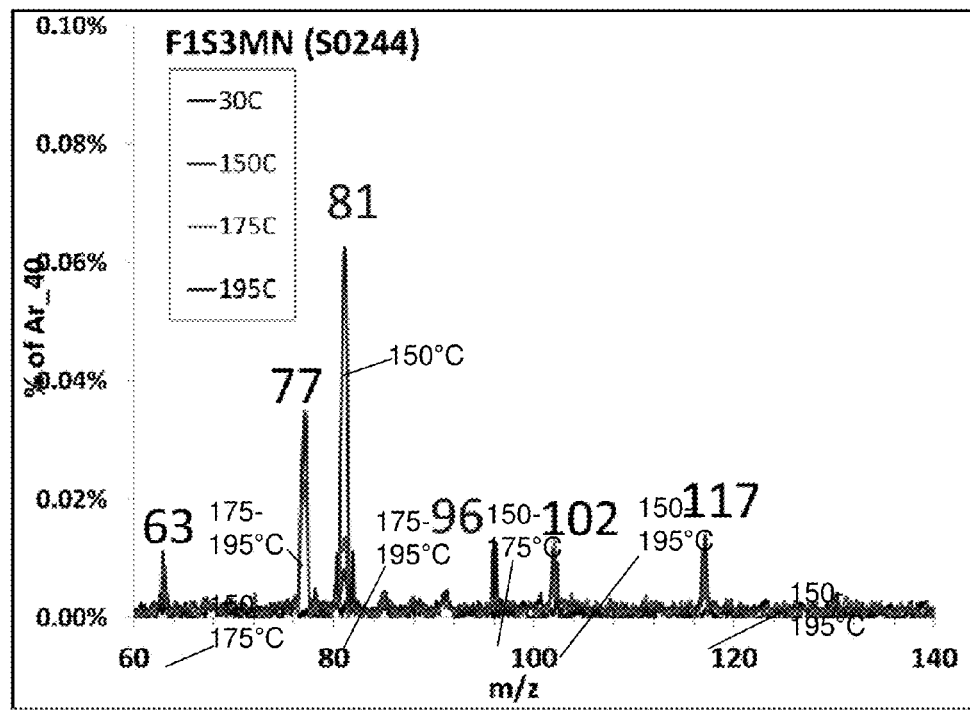
FIG. 9 depicts the thermal stability of neat $F1S_3MN$.

FIG. 9 depicts the thermal stability of neat F1S$_3$MN. F1S$_3$MN electrolyte was exposed to temperatures ranging from 30° C. to 195° C. and analyzed by mass spectrometry for decomposition products. The temperatures at which salient peaks appeared are annotated. Gas phase peaks were observed at temperatures ≥150° C. At 150° C., Me$_2$SiF$_2$ was observed (96/81 m/z), but other peaks were not associated with this product. $^1$H NMR analysis showed no fluorinated decomposition products and <0.5% hydrolysis.

The above data show that F1S$_3$MN is the most thermally stable OS solvent with LiPF$_6$.

Synthesis of DF1S$_3$MN:

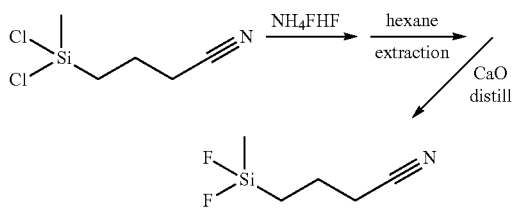

Commercial 3-cyanopropyldichloromethylsilane (CAS No. 1190-16-5; Sigma Aldrich, St. Louis, Mo., US) was fluorinated with ammonium bifluoride at room temperature. Cold hexane was then added to the mixture. The solid was filtered off and the solvent evaporated. Calcium oxide was added to the crude product. The solvent was distilled under vacuum between 35-45° C. at 0.4 Torr to yield the desired product in very high purity (~99.8%) and approximately 90% yield.

Synthesis of DF1S$_2$MN:

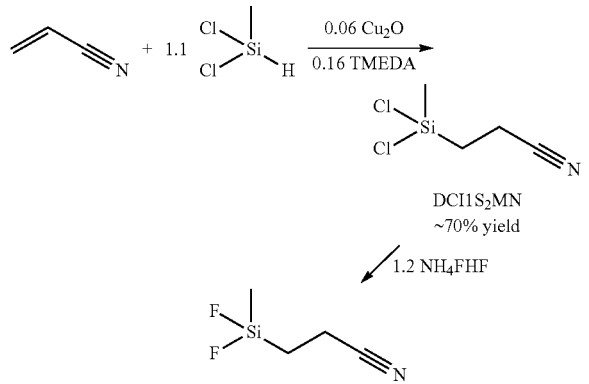

Acrylonitrile was mixed with N,N,N',N'-tetramethylethylenediamine and copper (I) oxide in a flask and heated to 60° C. Dichloromethylsilane was then added dropwise and refluxed overnight. After cooling to room temperature, the mixture was distilled under vacuum (43° C., 0.2 Torr) to yield the dichloro intermediate (DCl1S$_2$MN). The intermediate was fluorinated using 1.2 mol equivalents of ammonium hydrogen fluoride at room temperature or 1.2 mol equivalents of sodium hydrogen fluoride at 130° C. Dichloromethane was then added and the solid filtered off. The solvent was evaporated and the crude product was distilled under vacuum. Triethylamine and molecular sieves were added to the product and distilled under vacuum between 25-33° C. at 0.1 Torr to yield the desired product at extremely high purity (>99%) at approximately 75% yield.

Figure 10:
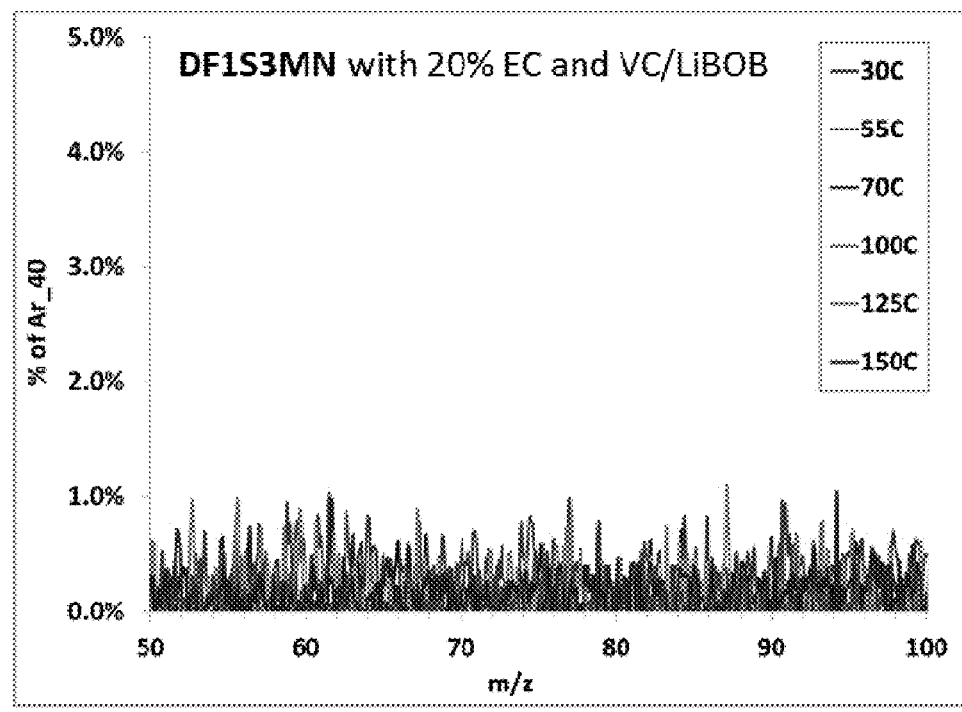
FIG. 10 depicts the thermal stability of $DF1S_3MN$ with 20% EC and VC/LiBOB.

Thermal Stability of DF1S$_3$MN:

FIG. 10 depicts the thermal stability of DF1S$_3$MN with LiPF$_6$. DF1S$_3$MN-LiPF$_6$ electrolyte (ZP990-01) was exposed to temperatures from 30° C. to 150° C. and analyzed by electron impact mass spectrometry (EI-MS) and nuclear magnetic resonance spectroscopy (NMR) for gas and liquid decomposition products, respectively. DF1S$_3$MN showed no significant gas and/or liquid phase decomposition up to 150° C.

Differential Scanning calorimetry (DSC) Evaluation for Thermal Abuse Tolerance:

DSC measurements were conducted with F1S$_3$MN and carbonate based electrolytes in the presence of de-lithiated cathode materials to evaluate potential thermal abuse tolerance effects that could translate to safety advantages in a full cell format. Higher onset temperature, lower total heat output and lower peak heat output are all effects that suggest improved thermal abuse behavior in full format cells.

Figure 11:
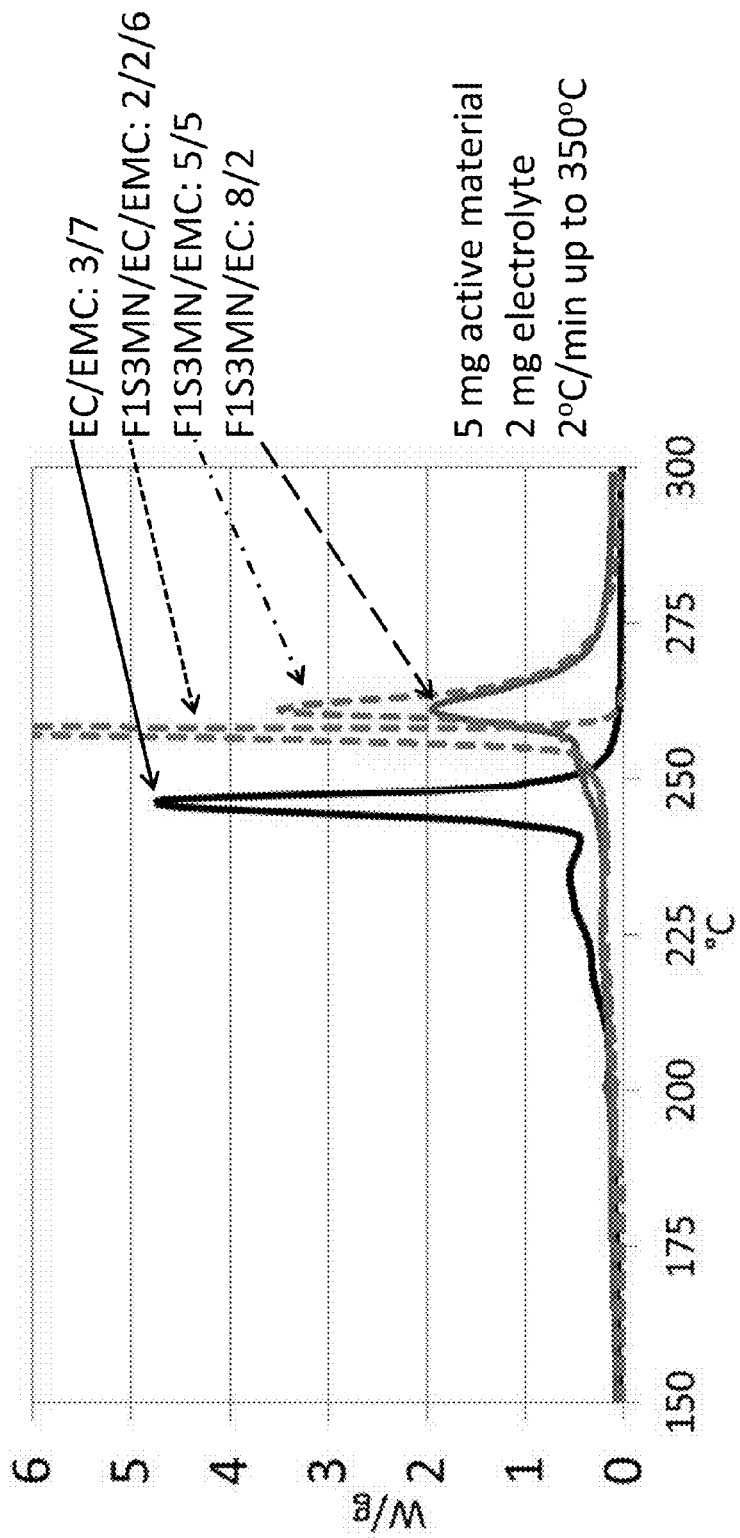
FIG. 11 depicts the enhanced stability of F1S3MN electrolytes compared to carbonate control electrolyte heated with de-lithiated NCA cathode.

FIG. 11 depicts the thermal stability of F1S$_3$MN with LiPF$_6$ and various carbonate co-solvents and is compared to a carbonate control electrolyte with LiPF$_6$. Cells containing each electrolyte were charged to 4.25V and then disassembled. The lithium nickel cobalt aluminum oxide (NCA) cathode was rinsed with diethylene carbonate and allowed to dry. Each sample containing 5 mg of active material and 2 mg of fresh electrolyte was hermetically sealed into a stainless steel DSC pan. DSC scans at a rate of 2° C./min showed that the carbonate control electrolyte reacted at a much lower onset temperature than any of the organosilicon electrolyte blends. Additionally, the electrolyte where organosilicon is substituted for EMC has a much lower peak heat output than the control electrolyte.

Preparation of Electrolytes:

Blending of electrolytes is completed inside a moisture-free (<5 ppm) and oxygen-free (<20 ppm) argon glove box. All electrolyte components, including solvents, salts, and additives have been properly dried before blending and are stored in the glove box. Solvent moisture is monitored periodically by Karl Fischer measurement to ensure moisture levels are maintained at <20 ppm. Generally, solvents are weighed first into a separate vial and mixed until homogeneous. 70% of the solvent is added to a volumetric flask. Lithium (or other) salt is added slowly and stirred by magnetic stir bar until completed dissolved. Any other additives (i.e. VC, LiBOB) are then added slowly and stirred until the solution is homogeneous. The stir bar is removed and a portion of the remaining solvent is added to complete the volumetric requirement. The stir bar is placed back into the volumetric flask and the electrolyte is stirred until homogeneous. After blending is complete the electrolyte is dispensed into a dried vial or alternate container for storage.

Figure 12:
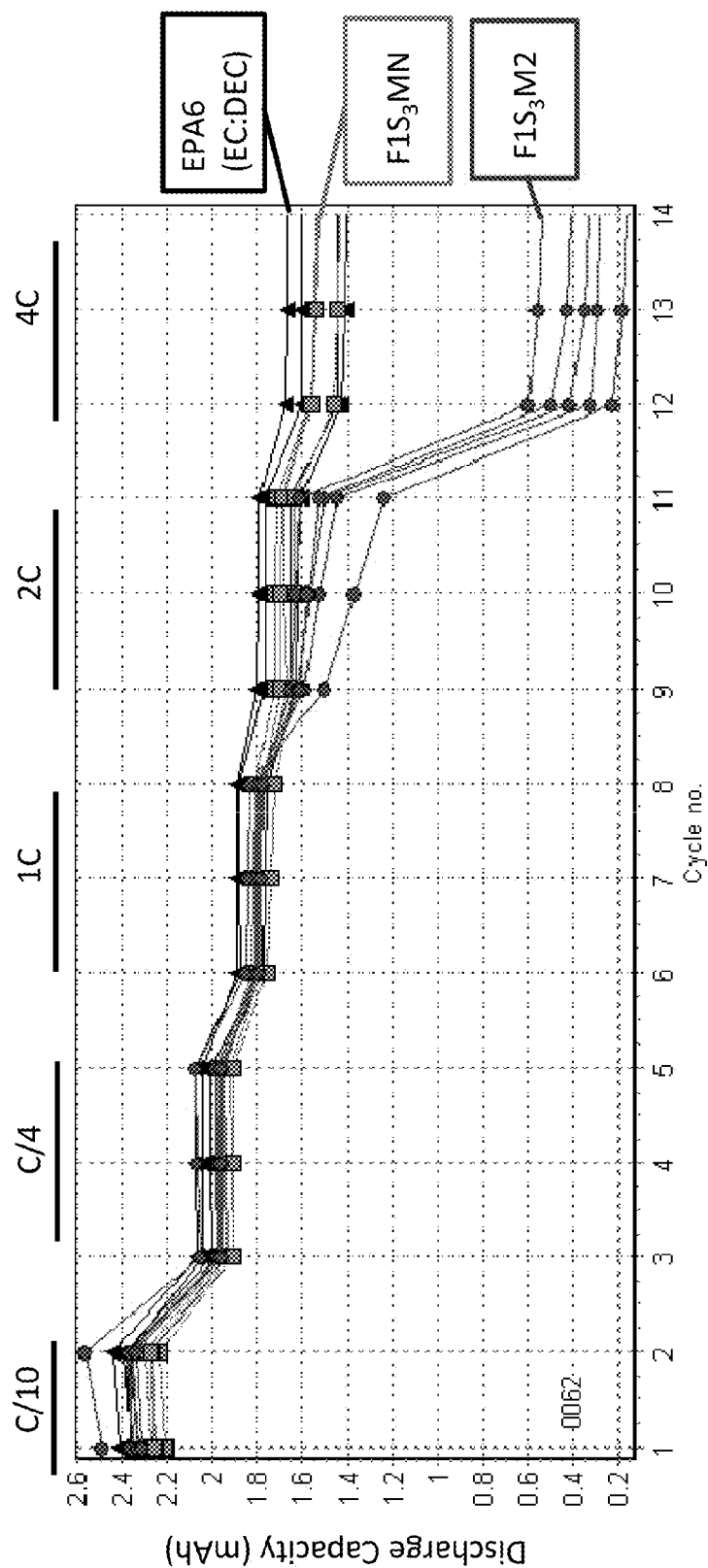
FIG. 12 depicts the discharge capacity of cells containing various electrolyte solvents at a variety of C-rates at 30° C.
Figure 13:
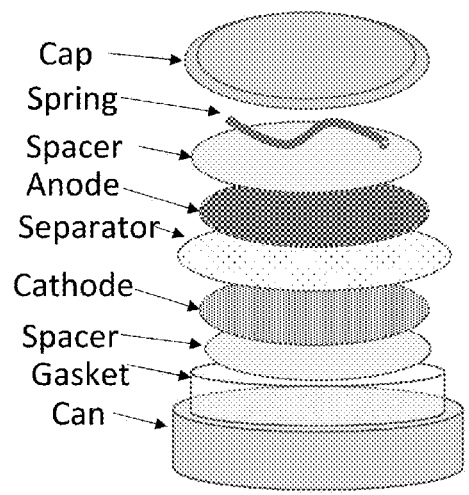
FIG. 13 depicts the construction of a test cell.

Performance of F1S$_3$MN in Lithium Ion Cells:

FIG. 12 depicts the discharge capacity at 30° C. of cells containing various electrolyte solvents. Three different electrolyte solvents were tested in Lithium Ion cells over a series of cycles at different C-rates in a 2032-size coin cell assembly (assembly stack as in FIG. 13) containing a graphite anode, a lithium nickel cobalt aluminum oxide (NCA) cathode, and "2500"-type separator from Celgard, LLC (Charlotte, N.C.). The three electrolyte solvents were: (1) control EPA6 carbonate electrolyte comprising 1:1 by volume ethylene carbonate (EC) and diethyl carbonate (DEC) (triangles); (2) an F1S$_3$MN-based electrolyte comprising 79% F1S$_3$MN, 20% EC, 1 M LiPF$_6$, and solid electrolyte interphase (SEI)-forming additives (squares); and (3) an F1S₃M2-based electrolyte, comprising 79% F1S₃M2, 20% EC, 1 M LiPF₆, and SEI-forming additives (circles). As shown in FIG. 12, the F1S₃MN-based electrolyte is equivalent to EPA6 at the 4C rate.

Figure 14:
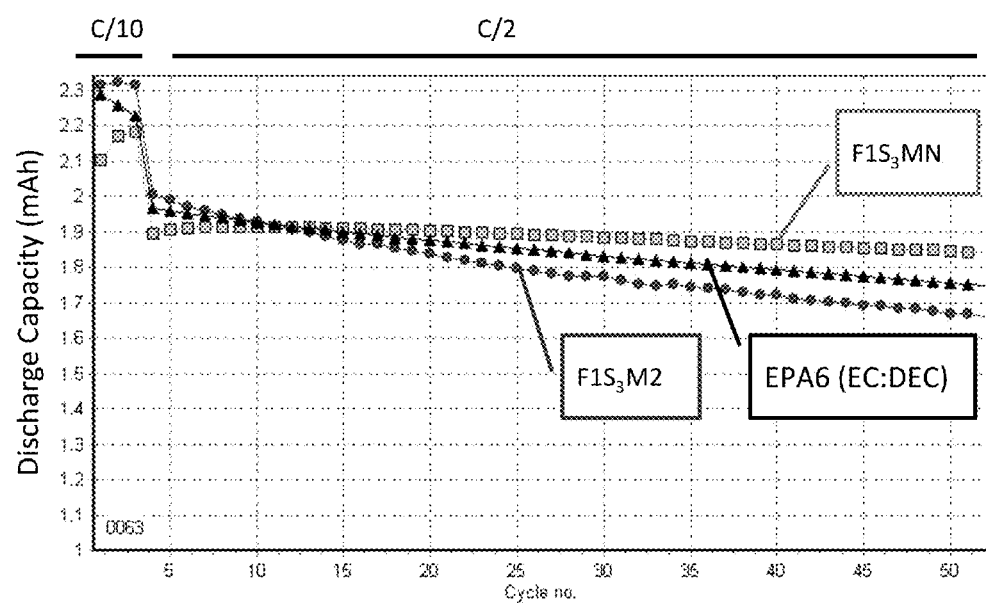
FIG. 14 depicts the discharge capacity of cells containing the same electrolyte solvents shown in FIG. 12 at a variety of C-rates at 55° C.

FIG. 14 depicts the discharge capacity at 55° C. of cells containing the same electrolytes as shown in, and described for FIG. 12. The cells were assembled in the same manner and cycled at a C/2 rate. As shown in FIG. 14, the F1S₃MN-based solvent had improved cycling stability at 55° C. compared to both the carbonate control and the F1S₃M2-based electrolyte.

Figure 15:
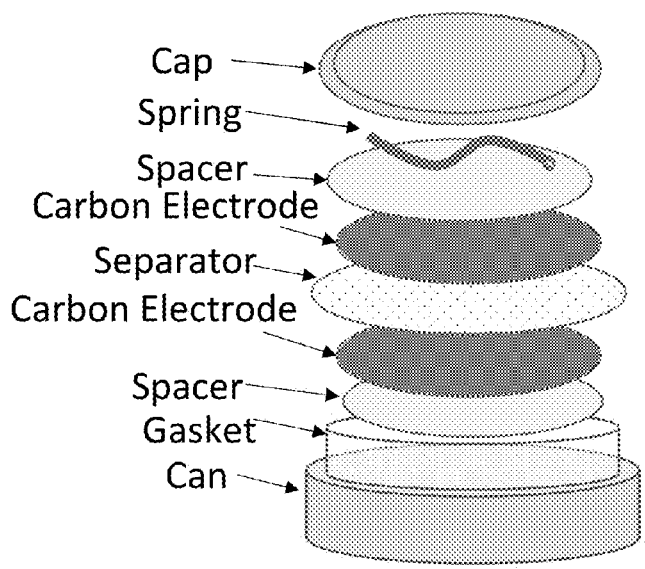
FIG. 15 depicts the construction of an EDLC device.

Performance of F1S₃MN and DF1S₂MN in Electrical Double-Layer Capacitors Cells:

Symmetric electrical double layer capacitors (EDLC) were assembled into CR2032 coin cells as depicted in FIG. 15. A glass fiber separator (AP40, Merck Millipore) was sandwiched between two pieces of AC cloth electrode, with 100 μL electrolyte added to the separator. Tetraethylammonium tetrafluoroborate (TEA-BF₄, Alfa Aesar, 99%) and tetrabutylphosphonium hexafluorophosphate (TBP-PF₆, Sigma Aldrich, ≥99.0%) were used as the salts. Organosilicon solvents of F1S₃MN (99.4%) and DF1S₂MN (99.8%) were made by Silatronix. Acetonitrile (AN, Sigma Aldrich, anhydrous, 99.8%) was used as a co-solvent. Zorflex FM10 100% activated carbon (AC) cloth from Calgon carbon was used for both electrodes. FM10 has 1000-2000 m2/g surface area, 0.5 mm thickness, and 120 g/m2 area density. The AC cloth was punched to 15 mm diameter discs, and used directly as electrodes without any binder or conductive additives.

The performance of EDLC cells was tested by cyclic voltammetry (CV) using a Biologic BMP300 potentiostat. The temperature as control in an oven with variation as ±0.1° C. The cyclic voltammetry (CV) responses of the EDLC cells was conducted between 0 and 3 V at a scan rate of 10 mV/s. A normalized specific capacitance, C, was derived according to the following equation [1,2]:

$$C = \frac{i}{mv}$$

where i is the current, v is the scan rate, m is the mass of one electrode.

Figure 16:
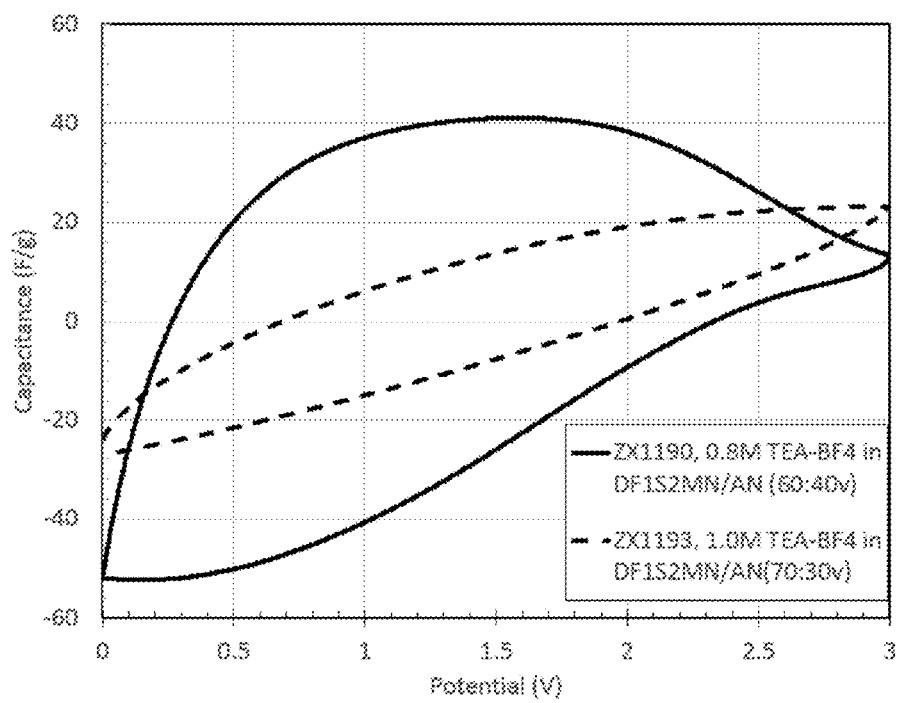
FIG. 16 depicts the performance of an EDLC device containing DF1S2MN electrolyte with TEA-BF4.

FIG. 16 shows the cyclic voltammograms of EDLC cells with OS electrolytes containing TEA-BF₄ salt. Electrolyte ZX1193 included 1.0M TEA-BF₄ dissolved in 70 volume percent DF1S₂MN and 30 volume percent acetonitrile. Electrolyte ZX1190 included 0.8M TEA-BF₄ dissolved into blended DF1S₂MN and acetonitrile solvents, 60:40 by volume. The EDLC cells with both electrolyte formulations showed the regular and symmetric features to the 0 horizontal axis, indicating a non-redox or faradic properties of the cell.

Figure 17:
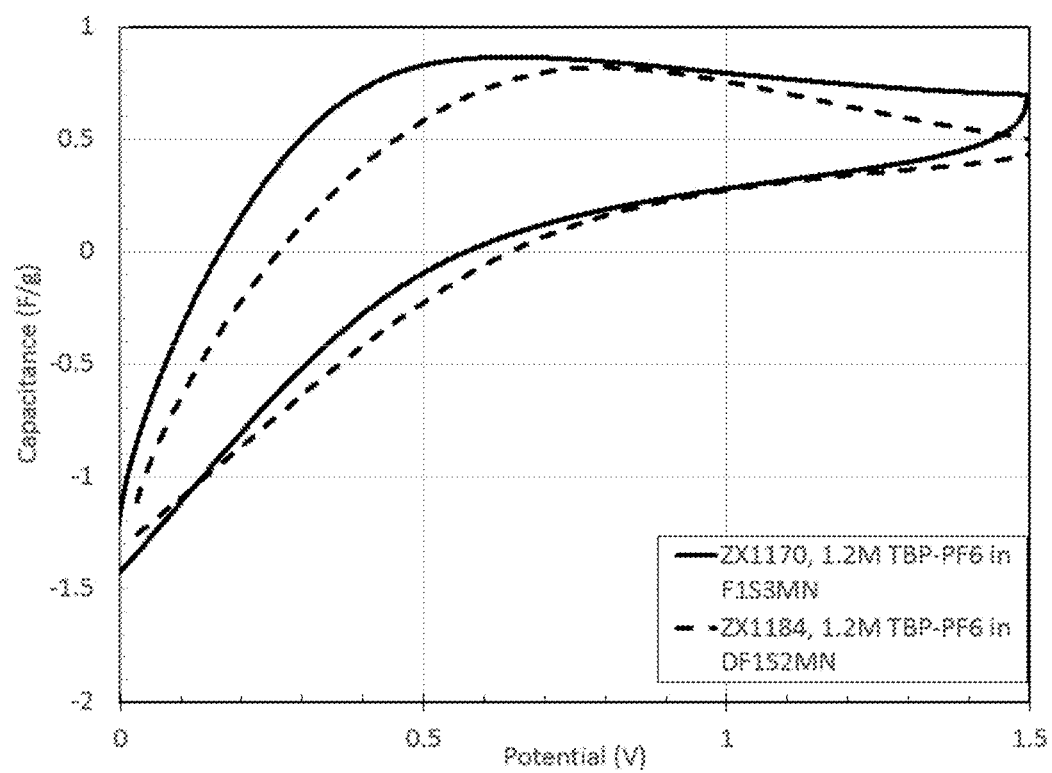
FIG. 17 depicts the performance of an EDLC device containing various electrolyte solvents with TBP-PF6.

FIG. 17 shows the cyclic voltammograms of EDLC cells with ZX1170 electrolyte and ZX1184 electrolyte containing TBP-PF₆ salt. Electrolyte ZX1170 has 1.2M TBP-PF₆ dissolved into F1S₃MN, and electrolyte ZX1184 has 1.2M TBP-PF₆ dissolved into DF1S₂MN. The non-redox or faradic properties can also be observed from the EDLC cells with both electrolyte ZX1170 and ZX1184 formulations.

1ND1N Synthesis:

Scheme 6 depicts a synthesis scheme for 1ND1N. 1ND1N cannot be chemically dried with sodium (Na), calcium oxide (CaO), or calcium hydride (CaH₂).

Scheme 6

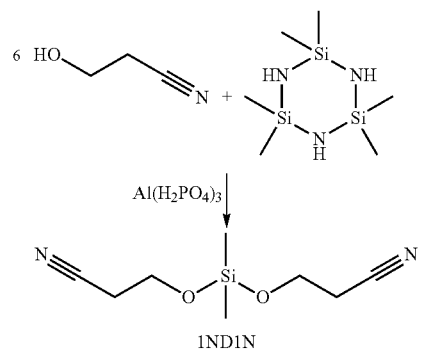

1ND1N (?) indicates text missing or illegible when filed

Electrochemical Stability of 1ND1N:

The molecular orbital diagram for 1ND1N and 1ND1, not shown, reveal the energy difference between the highest occupied molecular orbital (HOMO) and the lowest unoccupied molecular orbital (LUMO) for 1ND1N is 7.88 eV (LUMO=0.21 eV; HOMO=−7.88 eV) and for 1ND1 is 8.36 eV (LUMO=1.63 eV; HOMO=−6.73 eV). 1ND1N has great oxidation stability but lower reduction resistance than 1ND1.

Figure 18:
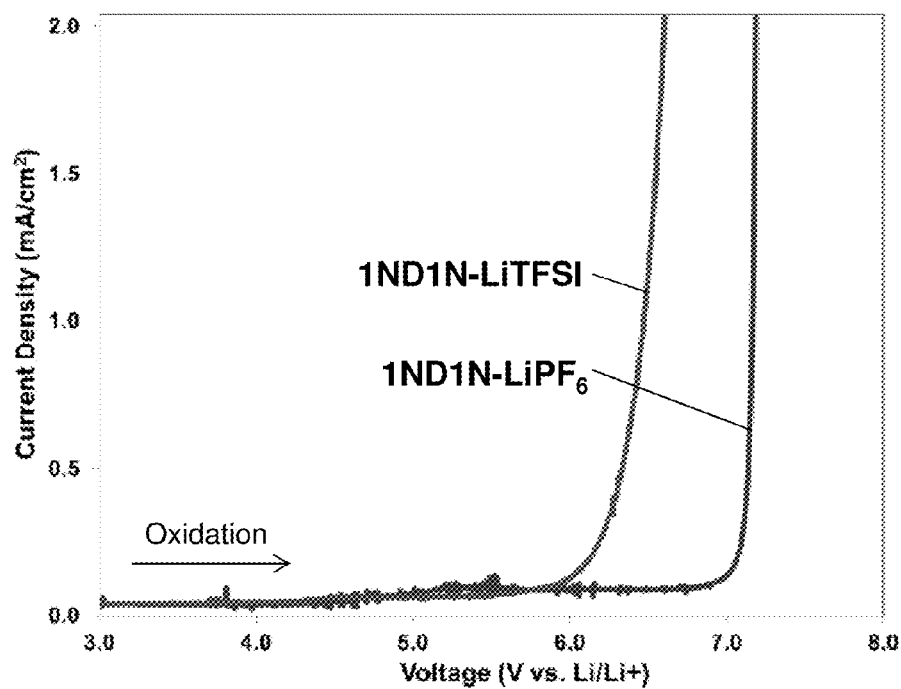
FIG. 18 depicts the oxidation stability of 1ND1N with 1M $LiPF_6$ or 1M LiTFSI in current density (mA/cm$^2$) versus voltage (V vs. Li/Li$^+$).

FIG. 18 depicts the oxidation stability of 1ND1N with 1M LiPF₆ or 1M LiTFSI in current density (mA/cm²) versus voltage (V vs. Li/Li⁺). The oxidation stability was tested at room temperature with a working electrode as Pt, a counter electrode as Li, a reference electrode as Li/Li⁺, and a sweep rate of 10 mV/s.

Figure 19:
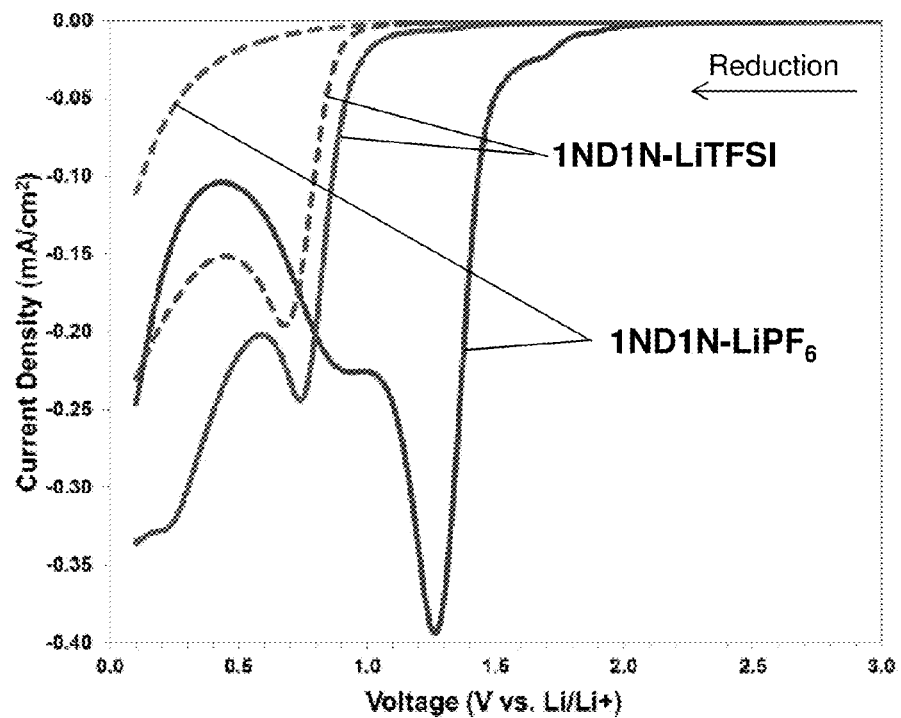
FIG. 19 depicts the reduction stability of 1ND1N with 1M LiPF$_6$ or 1M LiTFSI in current density (mA/cm$^2$) versus voltage (V vs. Li/Li$^+$).

FIG. 19 depicts the reduction stability of 1ND1N with 1M LiPF₆ or 1M LiTFSI in current density (mA/cm²) versus voltage (V vs. Li/Li⁺). The reduction stability was tested at room temperature with a working electrode as Pt, a counter electrode as Li, a reference electrode as Li/Li⁺, and a sweep rate of 10 mV/s. Two separate scans for each electrolyte are shown.

Figure 20A:
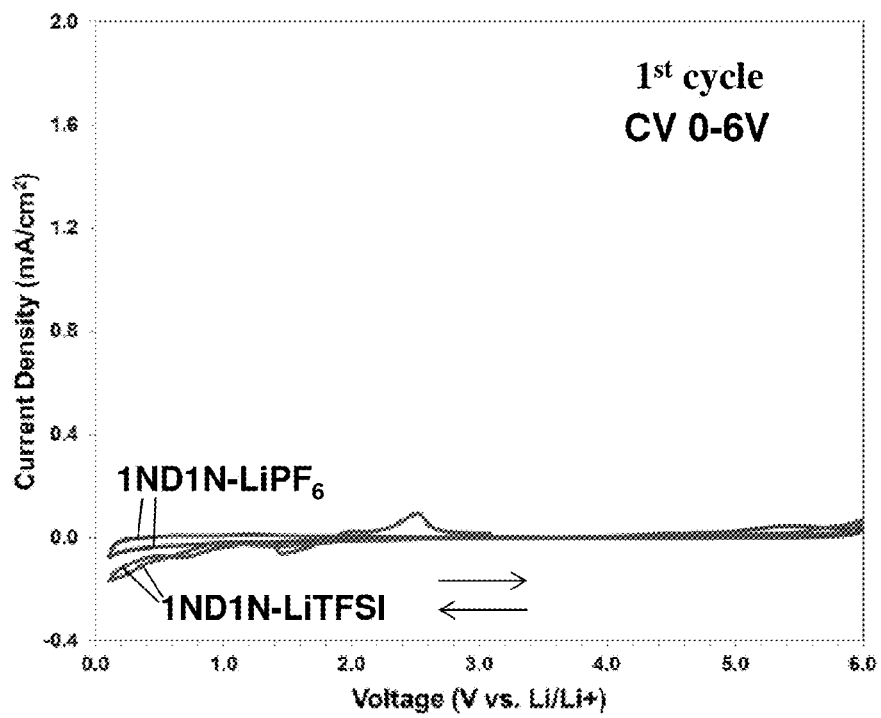
FIGS. 20A and 20B depict current density (mA/cm$^2$) versus voltage (V vs. Li/Li$^+$) for cycling scans with 1ND1N and 1M LiPF$_6$ or 1M LiTFSI from 0 to 6 V and from 6 to 0 V.
Figure 20B:
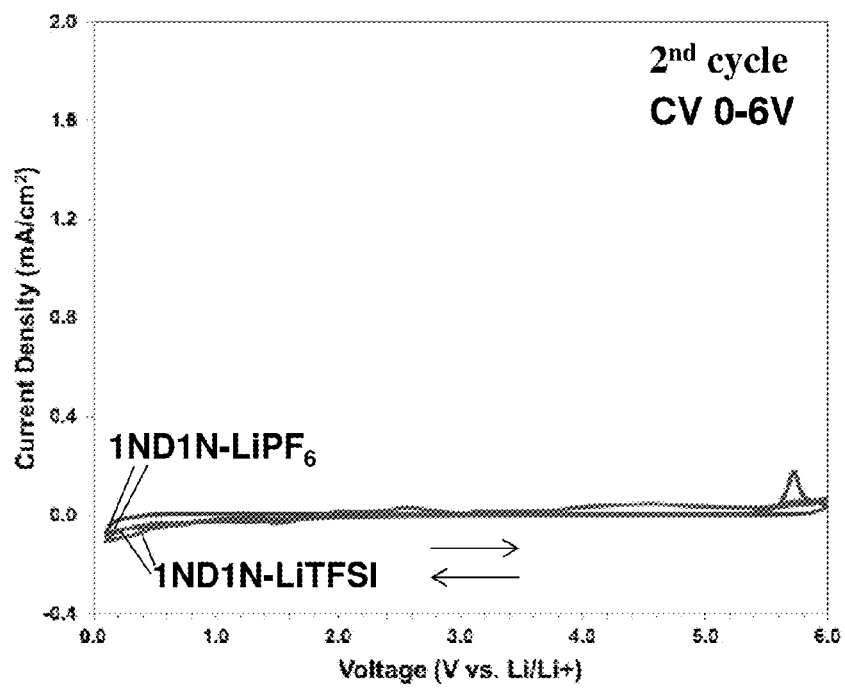

FIGS. 20A and 20B depict current density (mA/cm²) versus voltage (V vs. Li/Li⁺) for cycling scans with 1ND1N and 1M LiPF₆ or 1M LiTFSI from 0 to 6 V and from 6 to 0 V. FIG. 20A depicts a first cycle. FIG. 20B depicts a second cycle.

Figure 21A:
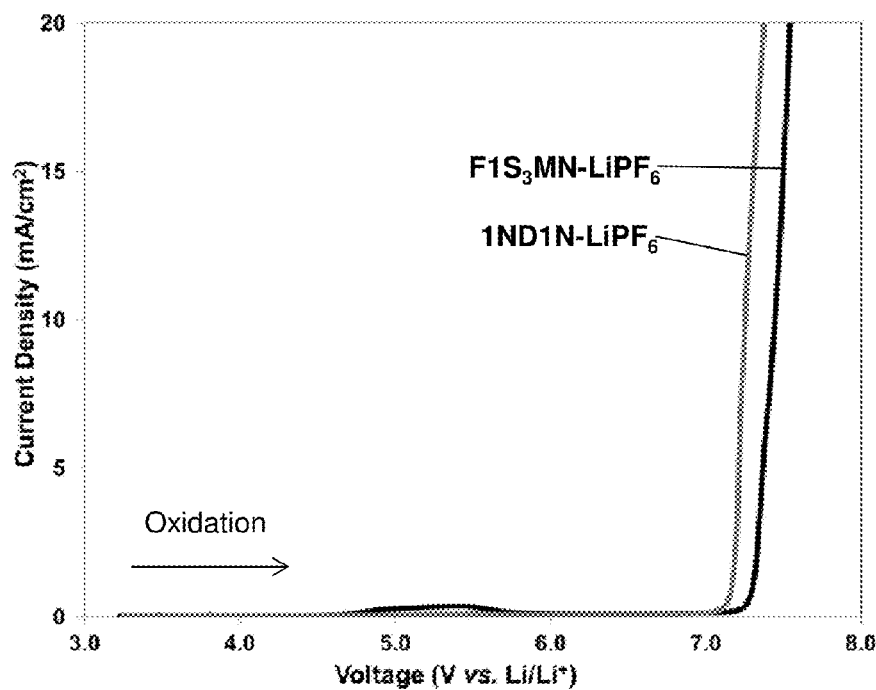
FIG. 21A depicts the oxidation stability of F1S$_3$MN or 1ND1N with 1M LiPF$_6$ in current density (mA/cm$^2$) versus voltage (V vs. Li/Li$^+$).
Figure 21B:
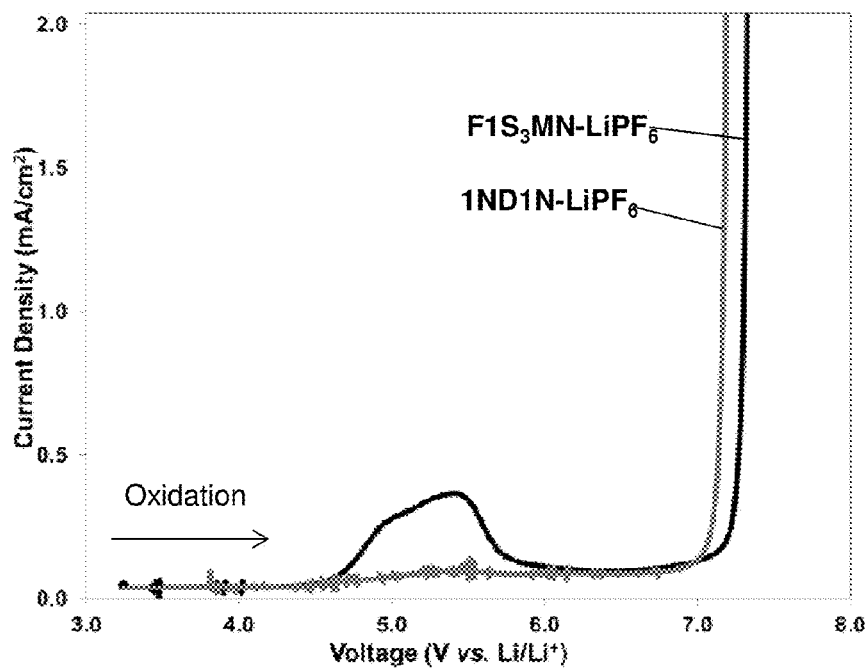
FIG. 21B depicts a close-up of the same data shown in FIG. 21A.

FIGS. 21A and 21B depict the oxidation stability of F1S₃MN or 1ND1N with 1M LiPF₆ in current density (mA/cm²) versus voltage (V vs. Li/Li⁺). The oxidation stability was tested at room temperature with a working electrode as Pt, a counter electrode as Li, a reference electrode as Li/Li⁺, and a sweep rate of 10 mV/s. FIG. 21B depicts a close-up of the same data shown in FIG. 21A. The F1S₃MN-LiPF₆ electrolyte had a current density of 1 mA/cm² at 7.3 V, and the 1ND1N-LiPF₆ electrolyte had a current density of 1 mA/cm² at 7.2 V.

Figure 22A:
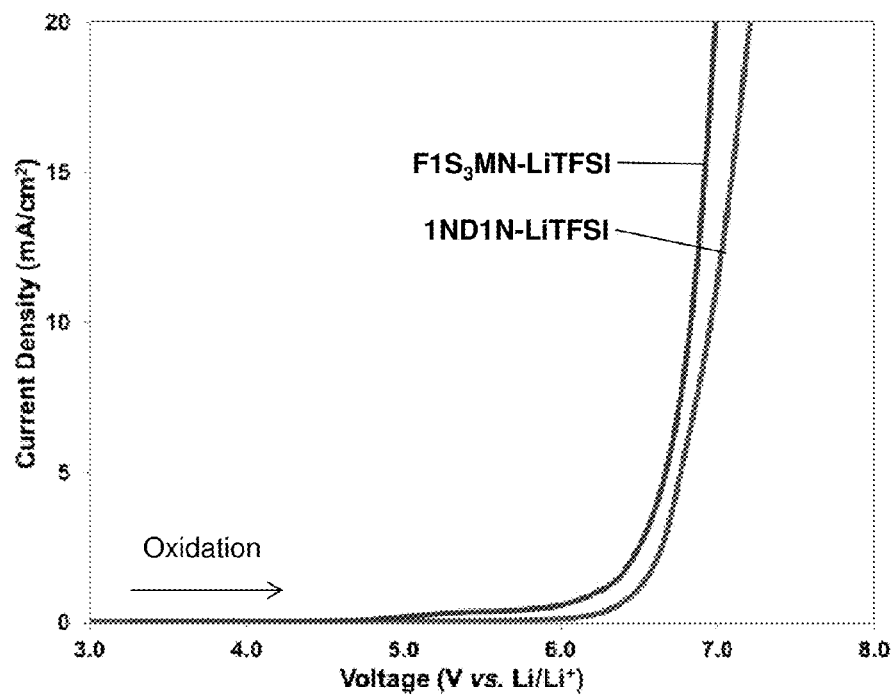
FIG. 22A depicts the oxidation stability of F1S$_3$MN or 1ND1N with 1M LiTFSI in current density (mA/cm$^2$) versus voltage (V vs. Li/Li$^+$).
Figure 22B:
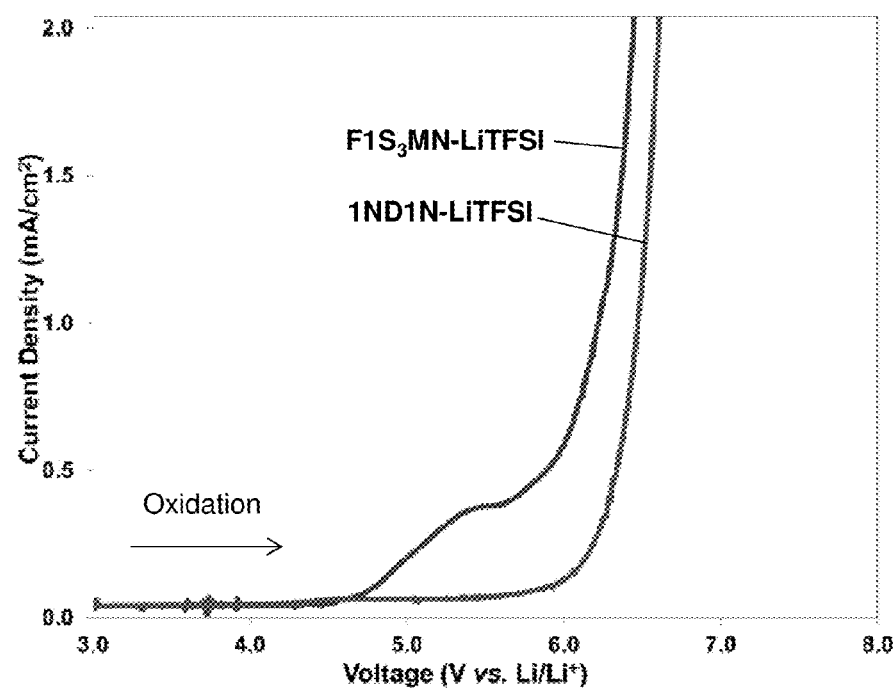
FIG. 22B depicts a close-up of the same data shown in FIG. 22A.

FIGS. 22A and 22B depict the oxidation stability of F1S₃MN or 1ND1N with 1M LiTFSI in current density (mA/cm²) versus voltage (V vs. Li/Li⁺). The oxidation stability was tested at room temperature with a working electrode as Pt, a counter electrode as Li, a reference electrode as Li/Li⁺, and a sweep rate of 10 mV/s. FIG. 22B depicts a close-up of the same data shown in FIG. 22A. The F1S₃MN-LiTFSI electrolyte had a current density of 1 mA/cm² at 6.2 V, and the 1ND1N-LiTFSI electrolyte had a current density of 1 mA/cm² at 6.5 V.

Figure 23:
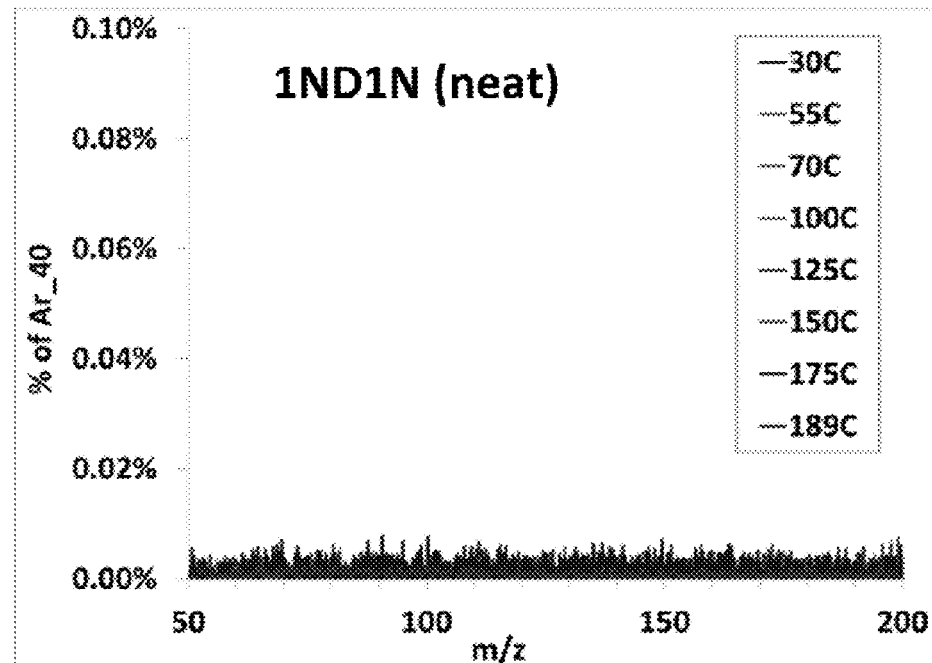
FIG. 23 is a mass spectrum illustrating the thermal stability of neat 1ND1N.

Thermal Stability of 1ND1N:

FIG. 23 depicts the thermal stability of neat 1ND1N. 1ND1N was exposed to temperatures ranging from 30° C. to 189° C. and analyzed by mass spectrometry for decomposition products. 1ND1N showed no liquid or gas phase decomposition products up to 189° C. $^1$H NMR showed ~%5 decomposition.

Figure 24:
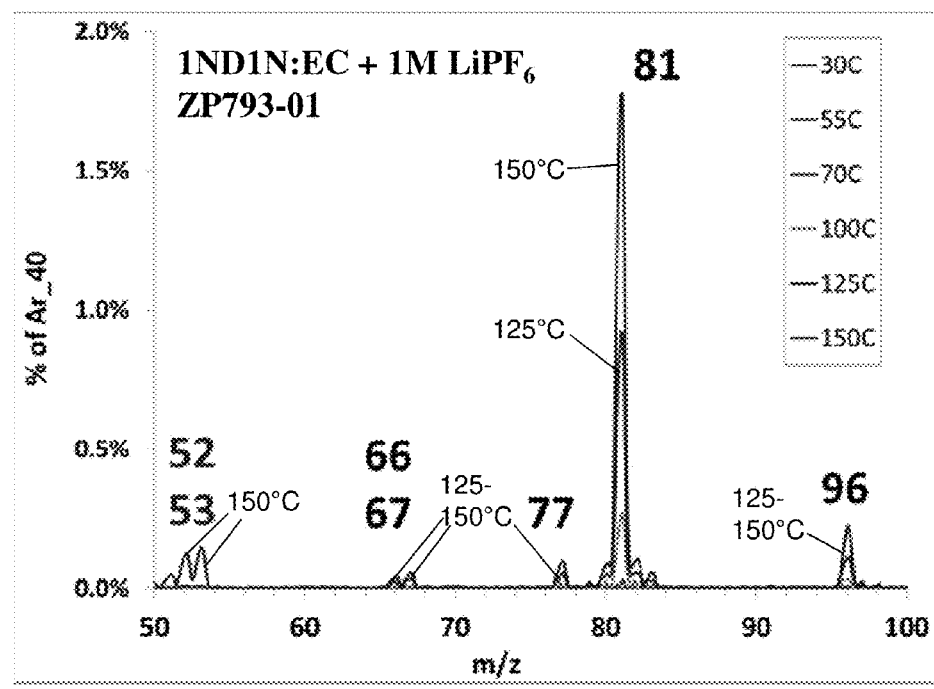
FIG. 24 is a mass spectrum illustrating the thermal stability of 1ND1N with LiPF$_6$.

FIG. 24 depicts the thermal stability of 1ND1N with LiPF$_6$. 1ND1N-LiPF$_6$ electrolyte was exposed to temperatures ranging from 30° C. to 150° C. and analyzed by mass spectrometry for decomposition products. The temperatures at which salient peaks appeared are annotated. 1ND1N showed gas phase decomposition ≥70° C., but no vigorous reaction was observed up to 150° C. Me$_2$SiF$_2$ (81 m/z) (96 g/mol) and a peak at 52/53 m/z suspected as being acrylonitrile (53 g/mol) appeared at a temperatures of 125-150° C. No 1,4-dioxane gas was observed at 150° C. $^1$H NMR analysis showed that 50.6% 1ND1N remained at 125° C. and 58% remained at 150° C. At 125° C., presence of 39.7% fluorinated product F1NM1N (vs. 2.3% in unheated sample), 1.6% Me$_2$SiF$_2$ (vs. 0% in unheated sample), and 2.95% hydrolysis (vs. 5.5% in unheated sample) was observed. At 150° C., presence of 41% fluorinated product F1NM1N (vs. 2.3% in unheated sample), 1.7% Me$_2$SiF$_2$ (vs. 0% in unheated sample), and 5.0% hydrolysis (vs. 5.5% in unheated sample) was observed.

Figure 25A:
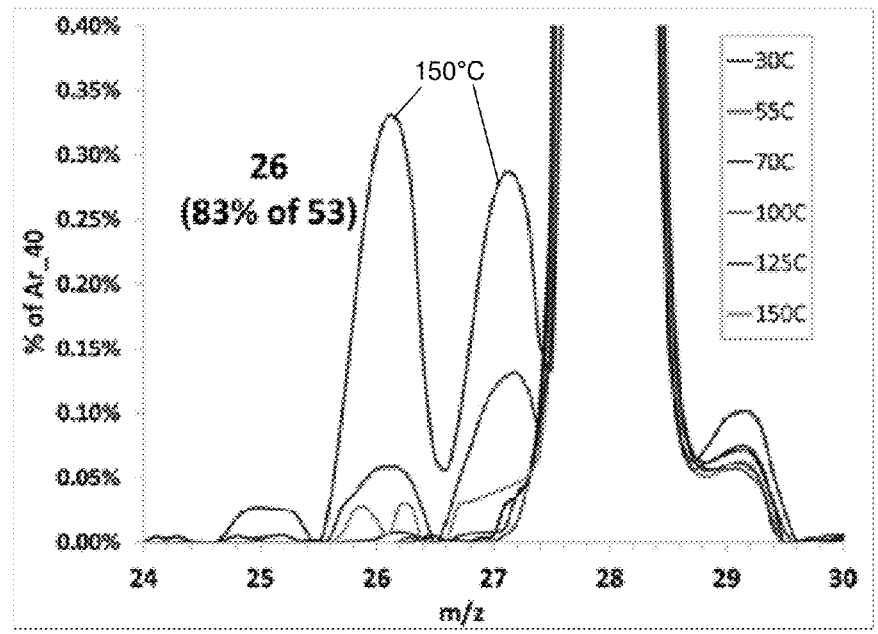
FIG. 25A depicts a close-up of the mass spectrum profile as described with respect to FIG. 24 from 24-30 m/z.
Figure 25B:
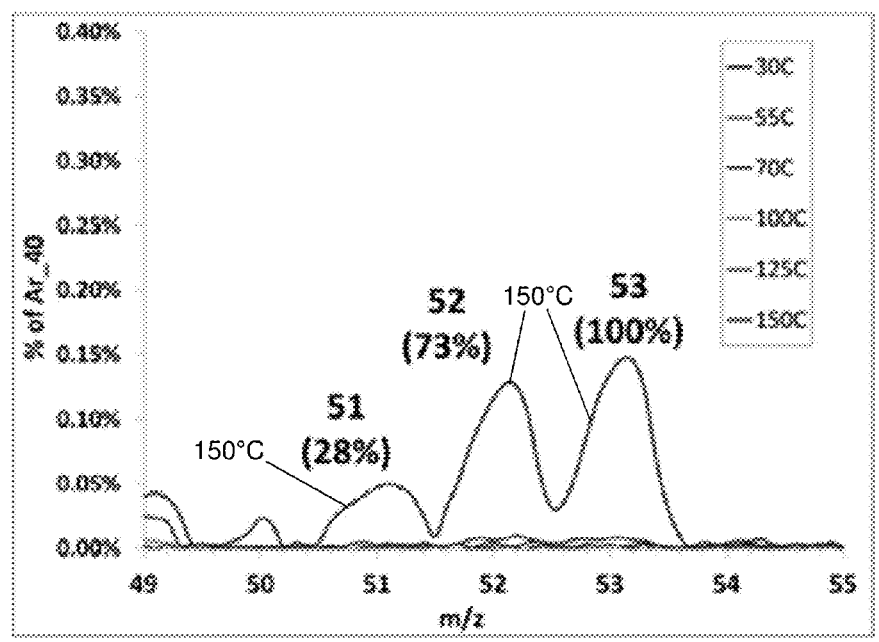
FIG. 25B depicts a close-up of the mass spectrum profile as described with respect to FIG. 24 from 49-55 m/z.

To identify the peaks observed at 52/53 m/z upon heating 1ND1N-LiPF$_6$ at 125-150° C., the mass spectrum profile for heated 1ND1N-LiPF$_6$ was compared with the mass spectrum profiles of National Institute of Standards and Technology (NIST) standards for 2-propenenitrile and hydrogen cyanide. FIG. 25A depicts a close-up of the mass spectrum profile as described with respect to FIG. 24 from 24-30 m/z. FIG. 25B depicts a close-up of the mass spectrum profile as described with respect to FIG. 24 from 49-55 m/z. The temperatures at which salient peaks in FIGS. 25A and 25B appeared are annotated. The peaks at 51, 52, and 53 m/z in FIG. 25B indicate that acrylonitrile is likely present. The presence of HCN cannot be definitively confirmed or disconfirmed due to the presence of peaks at 26 and 27 m/z in the NIST spectra. The spectrum in FIG. 25A shows a greater peak intensity at 26 m/z compared to 27 m/z, which supports the presence of acrylonitrile. However, the magnitude of the peak at 27 m/z is greater than expected for acrylonitrile alone.

Figure 26:
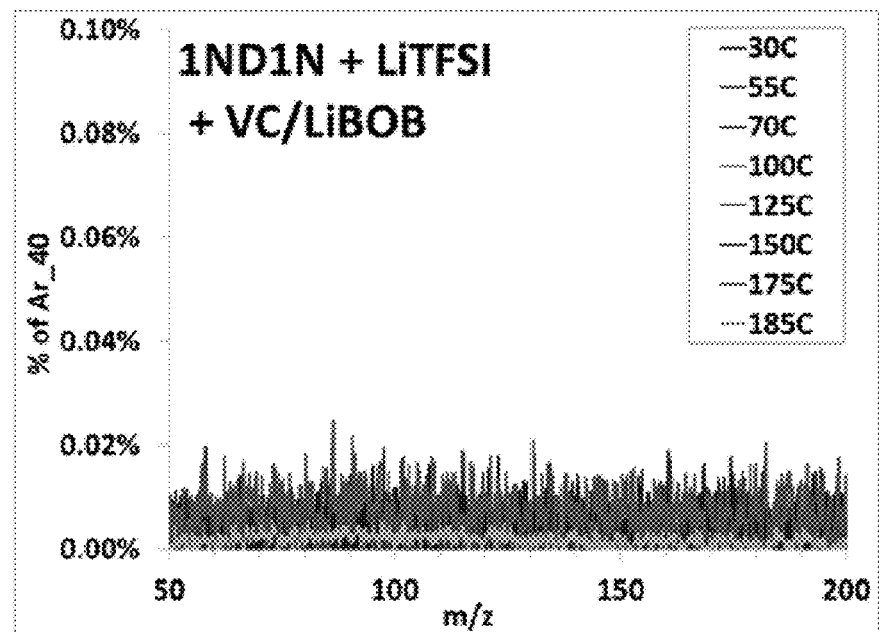
FIG. 26 depicts the thermal stability of 1ND1N with LiTFSI, vinylene carbonate (VC) and lithium bis(oxalato) borate (LiBOB).

FIG. 26 depicts the thermal stability of 1ND1N with LiTFSI, vinylene carbonate (VC) and lithium bis(oxalato) borate (LiBOB). 1ND1N-LiTFSI-VC-LiBOB was exposed to temperatures ranging from 30° C. to 185° C. and analyzed by mass spectrometry for decomposition products. 1ND1N-LiTFSI-VC-LiBOB showed no gas phase decomposition products up to 185° C. $^1$H NMR showed an increase in hydrolysis from 3% (in the unheated sample) to 18.7% (after heating), which was likely due to a delay before the NMR analysis was performed.

Figure 27:
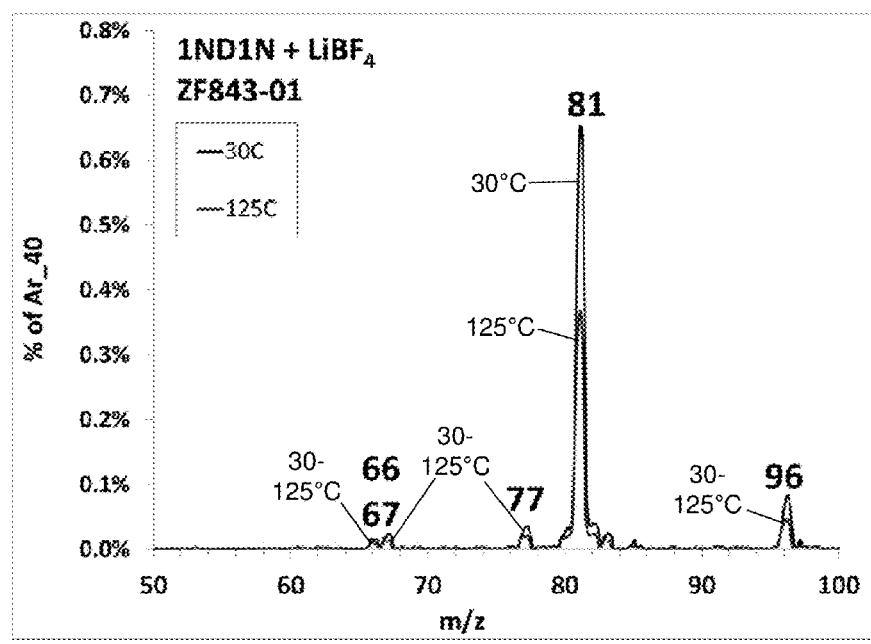
FIG. 27 depicts the thermal stability of 1ND1N with LiBF$_4$.

FIG. 27 depicts the thermal stability of 1ND1N with LiBF$_4$. 1ND1N-LiBF$_4$ was exposed to temperatures ranging from 30° C. to 125° C. and analyzed by mass spectrometry for decomposition products. The temperatures at which salient peaks appeared are annotated. Gas phase products evolved at ≥30° C. As expected, Me$_2$SiF$_2$ (81 m/z) (96 g/mol) was observed. No acrylonitrile was observed. $^1$H NMR showed 3.7% hydrolysis and 34.2% fluorinated products (3 sets of peaks). $^{19}$F NMR showed that all F in the system was bonded to Si. No BF$_4$ remained. There was insufficient F to fully decompose 1ND1N (~5M 1ND1N versus 4 M F).

While no acrylonitrile was observed by mass spectrometry in heated 1ND1N-LiBF$_4$ samples, it was observed in unheated control (70 ppm). This indicates 1ND1N is not stable with LiBF$_4$ at room temperature. NMR analysis revealed that heating does little to increase decomposition, as shown in the following table:

|  | $^1$H (MeSi peak) | |
| --- | --- | --- |
|  | hydrolysis | fluorination |
| Before Heating | 3% | 43% |
| After Heating | 4% | 34% |

Figure 28:
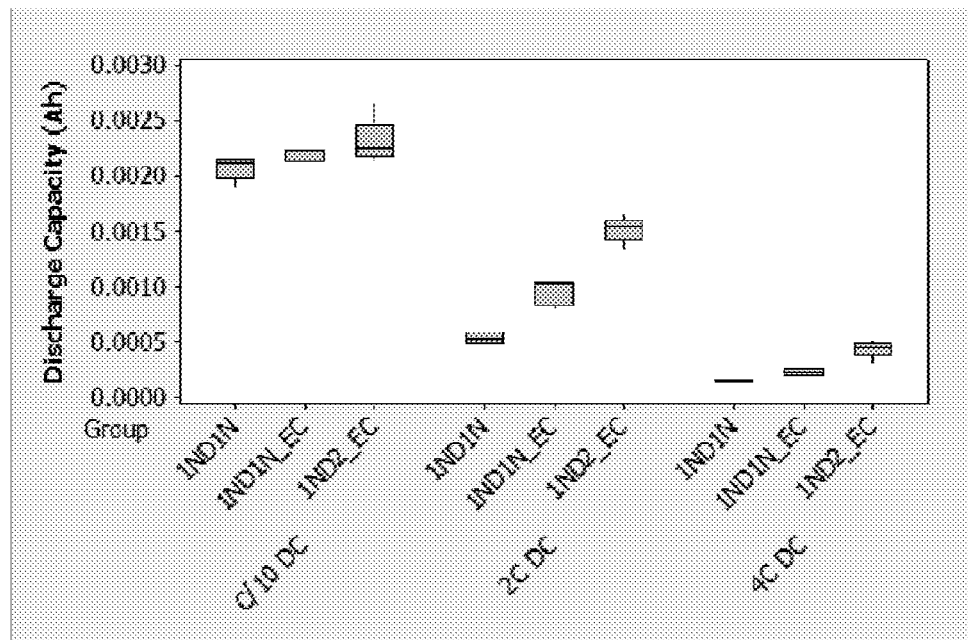
FIG. 28 depicts the discharge capacity of cells containing various electrolytes at a variety of C-rates.

Performance of 1ND1N in Cells:

FIG. 28 depicts the discharge capacity of cells containing various electrolytes at a variety of C-rates. The electrolyte solvents were: (1) 1ND1N; (2) 1ND1N with 20% ethylene carbonate (EC) co-solvent (1ND1N_EC); and (3) 1ND2 with 20% EC co-solvent (1ND2_EC). All formulations also contained SEI-forming additives and 1 M LiPF$_6$ salt. As shown in FIG. 28, 20% EC co-solvent improved the performance of 1ND1N. With 20% EC co-solvent, 1ND1N showed diminished performance compared to 1ND2 at all C-rates.

Figure 29:
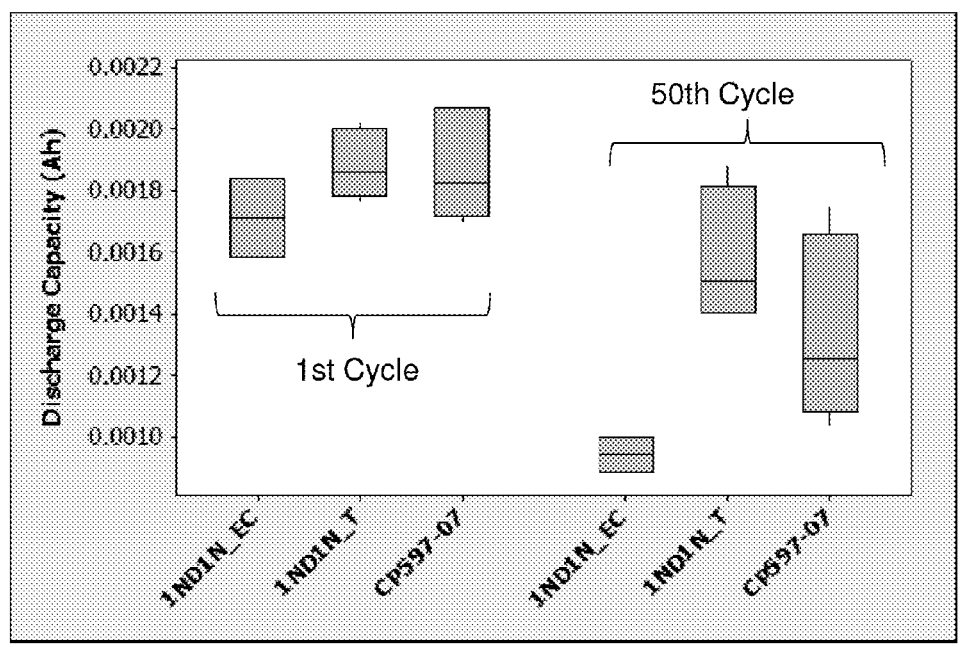
FIG. 29 depicts the discharge capacity of cells containing various other electrolyte solvents comparing the first cycle to the 50$^{th}$ cycle.

FIG. 29 depicts the discharge capacity of cells containing various other electrolyte solvents. The electrolyte solvents were: (1) 1ND1N with 20% EC co-solvent, 1 M LiPF$_6$ and SEI-forming additives (1ND1N-EC-LiPF$_6$, shown as 1ND1N_EC in FIG. 29); (2) 1ND1N with 20% EC co-solvent, 1 M LiTFSI and SEI-forming additives (1ND1N-EC-LiTFSI, shown as 1ND1N_T in FIG. 29); and (3) 1ND2 with 20% EC co-solvent, 1 M LiPF$_6$ and SEI-forming additives (1ND2-EC-LiPF$_6$, shown as CP597-07 in FIG. 29). The 1ND1N-EC-LiPF$_6$ combination and the 1ND1N-EC-LiTFSI combination showed performance comparable to the 1ND2-EC-LiPF$_6$ combination.

Figure 30A:
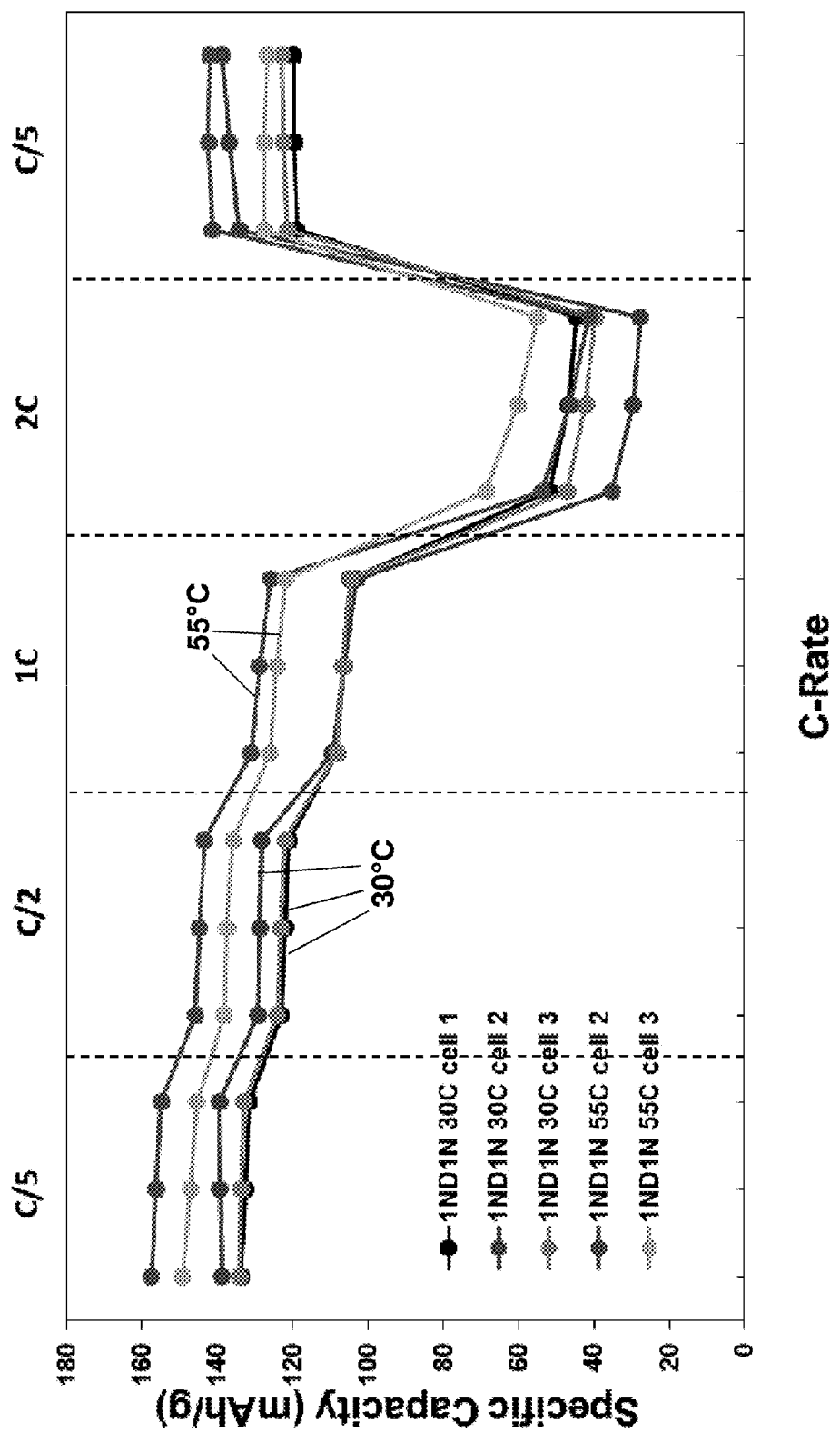
FIG. 30A depicts the discharge capacity of cells containing a 1ND1N-LiPF$_6$-based electrolyte at a variety of C-rates.
Figure 30B:
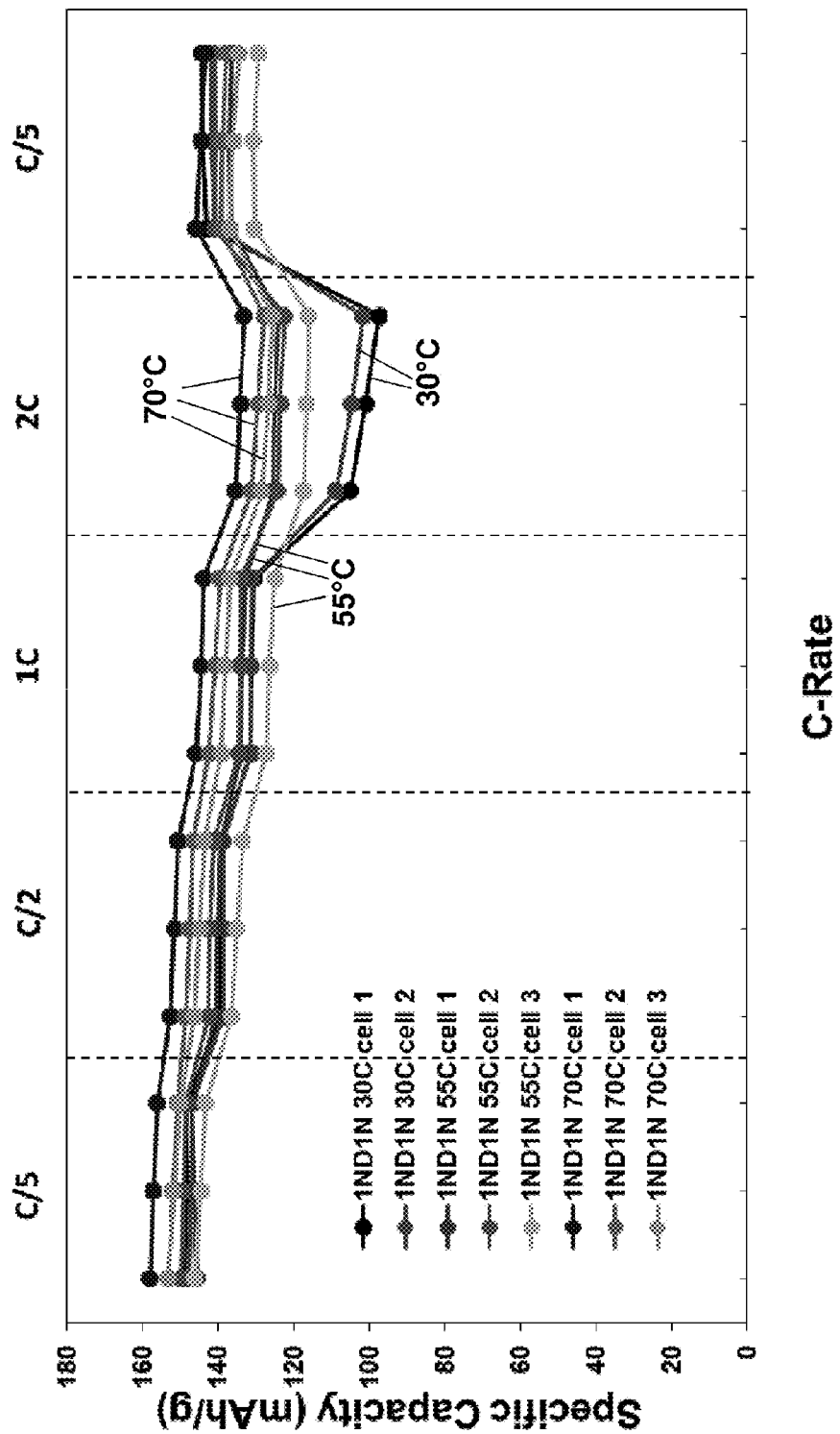
FIG. 30B depicts the discharge capacity of cells containing a 1ND1N-LiTFSI-based electrolyte at a variety of C-rates.
Figure 31:
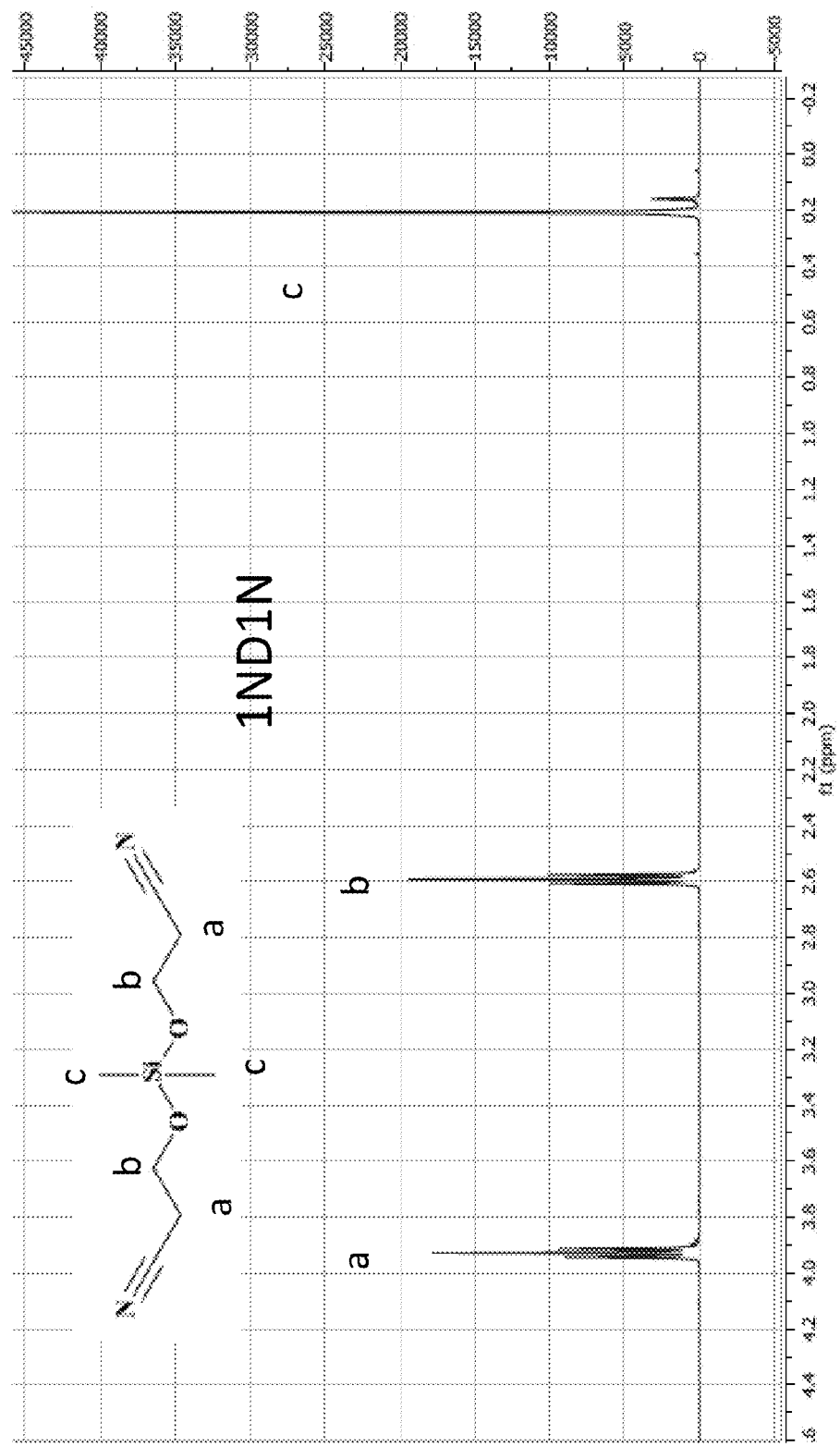
FIG. 31 is the $^1$H-NMR spectrum (in CDCl$_3$) of 1ND1N with peak assignments.
Figure 32:
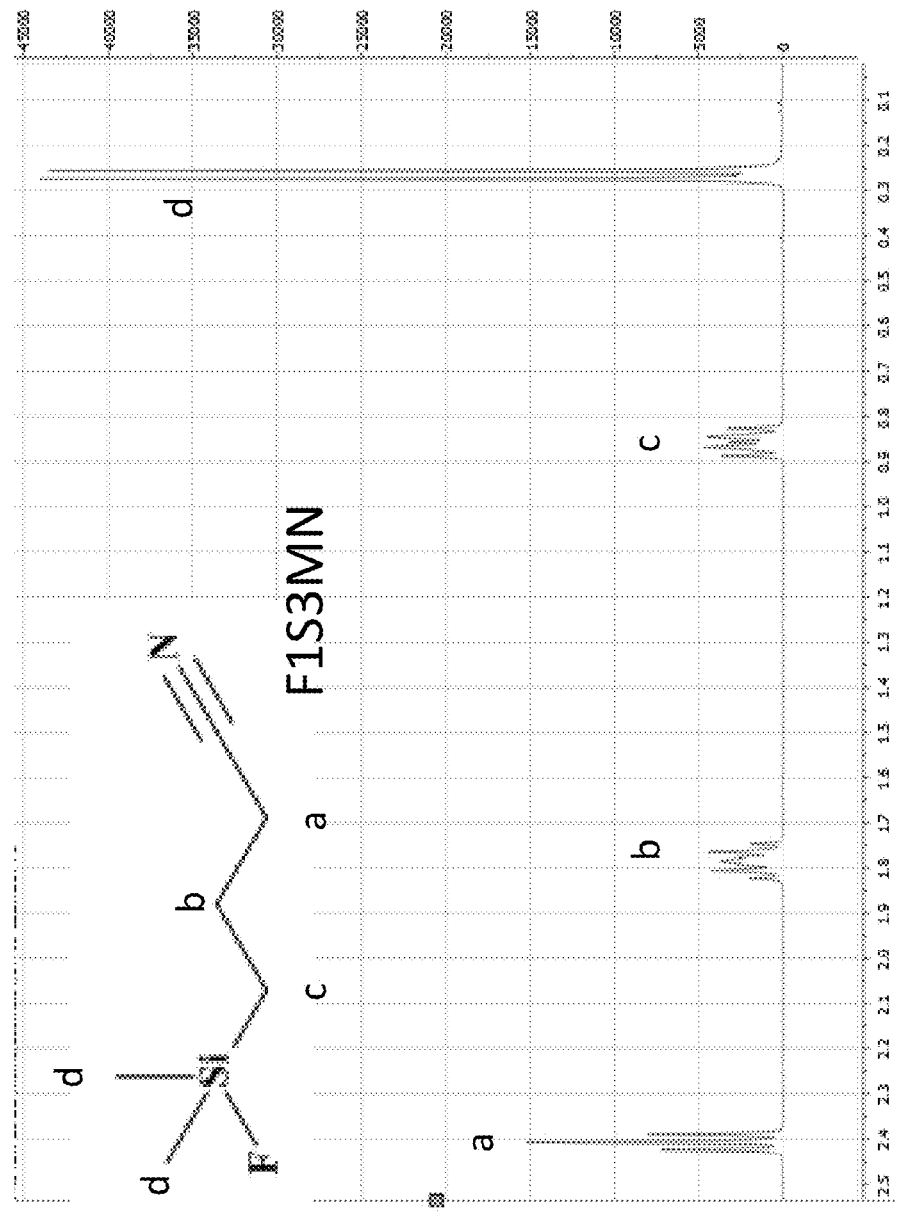
FIG. 32 is the $^1$H-NMR spectrum (in CDCl$_3$) of F1S$_3$MN with peak assignments.
Figure 33:
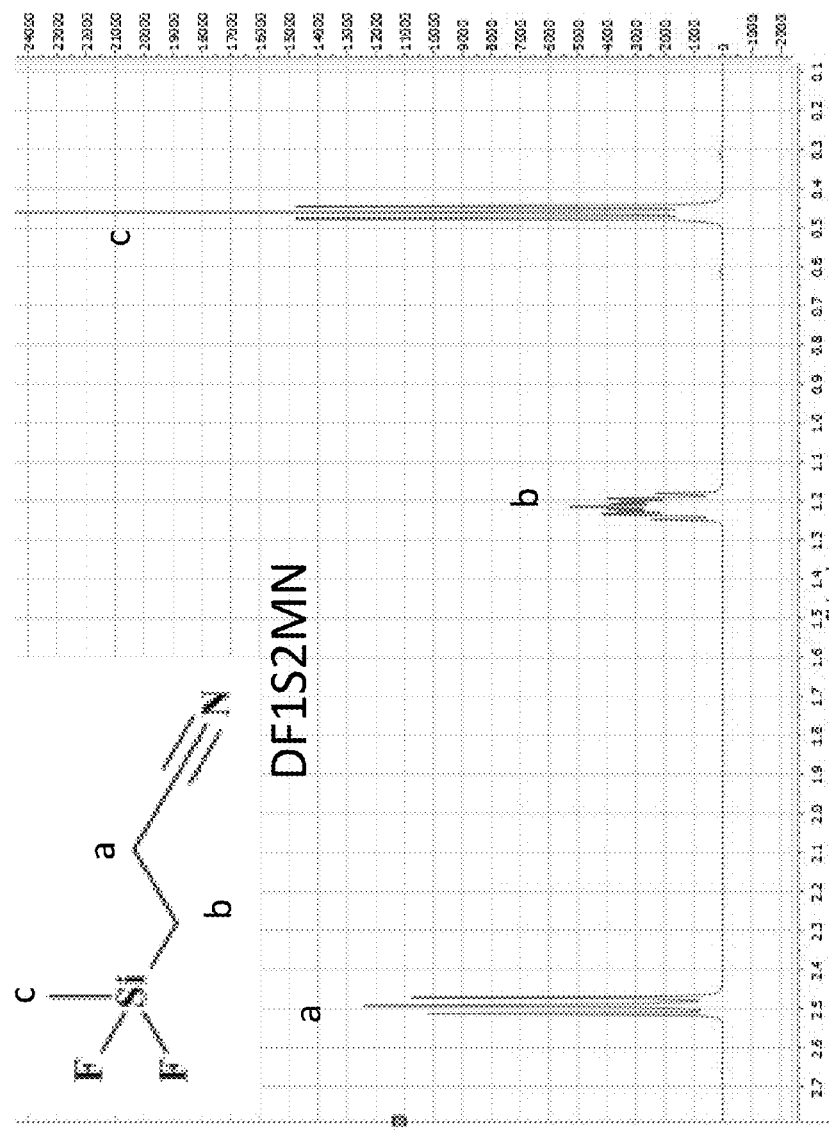
FIG. 33 is the $^1$H-NMR spectrum (in CDCl$_3$) of DF1S$_2$MN with peak assignments.
Figure 34:
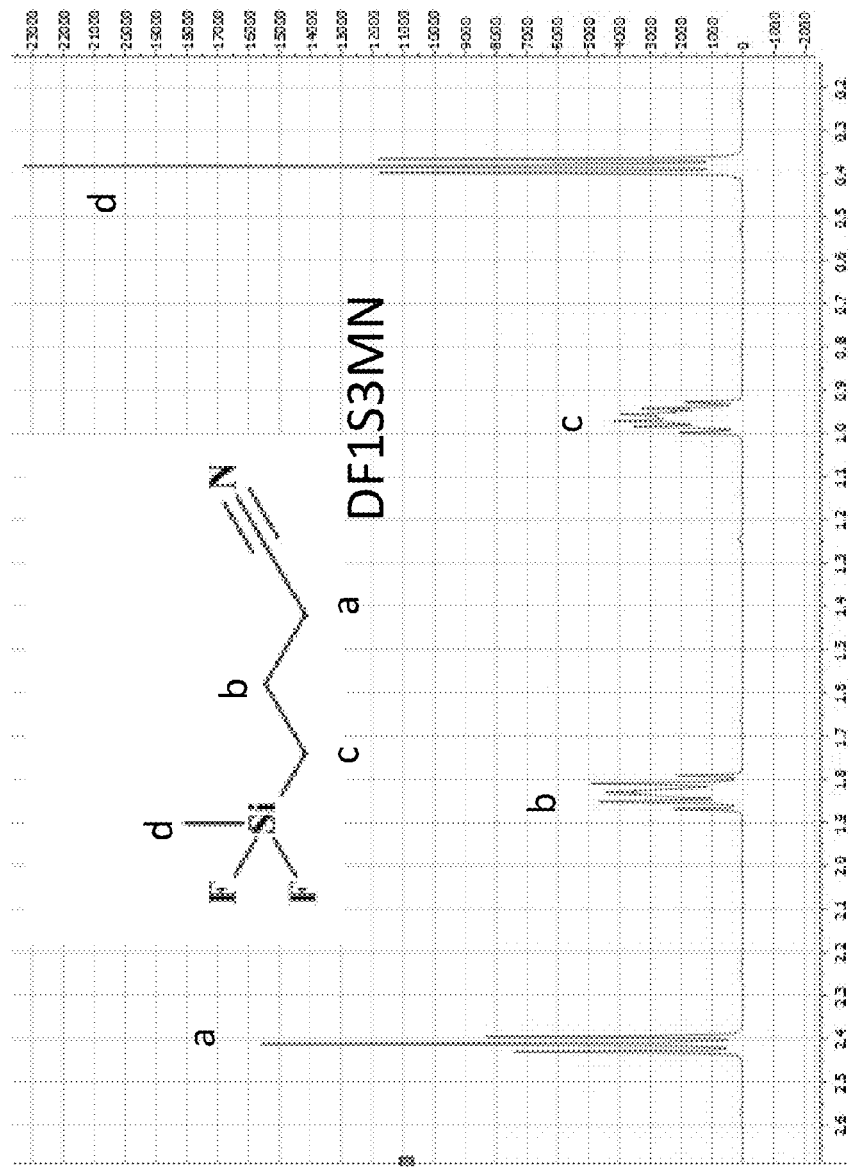
FIG. 34 is the $^1$H-NMR spectrum (in CDCl$_3$) of DF1S$_3$MN with peak assignments.
Figure 35:
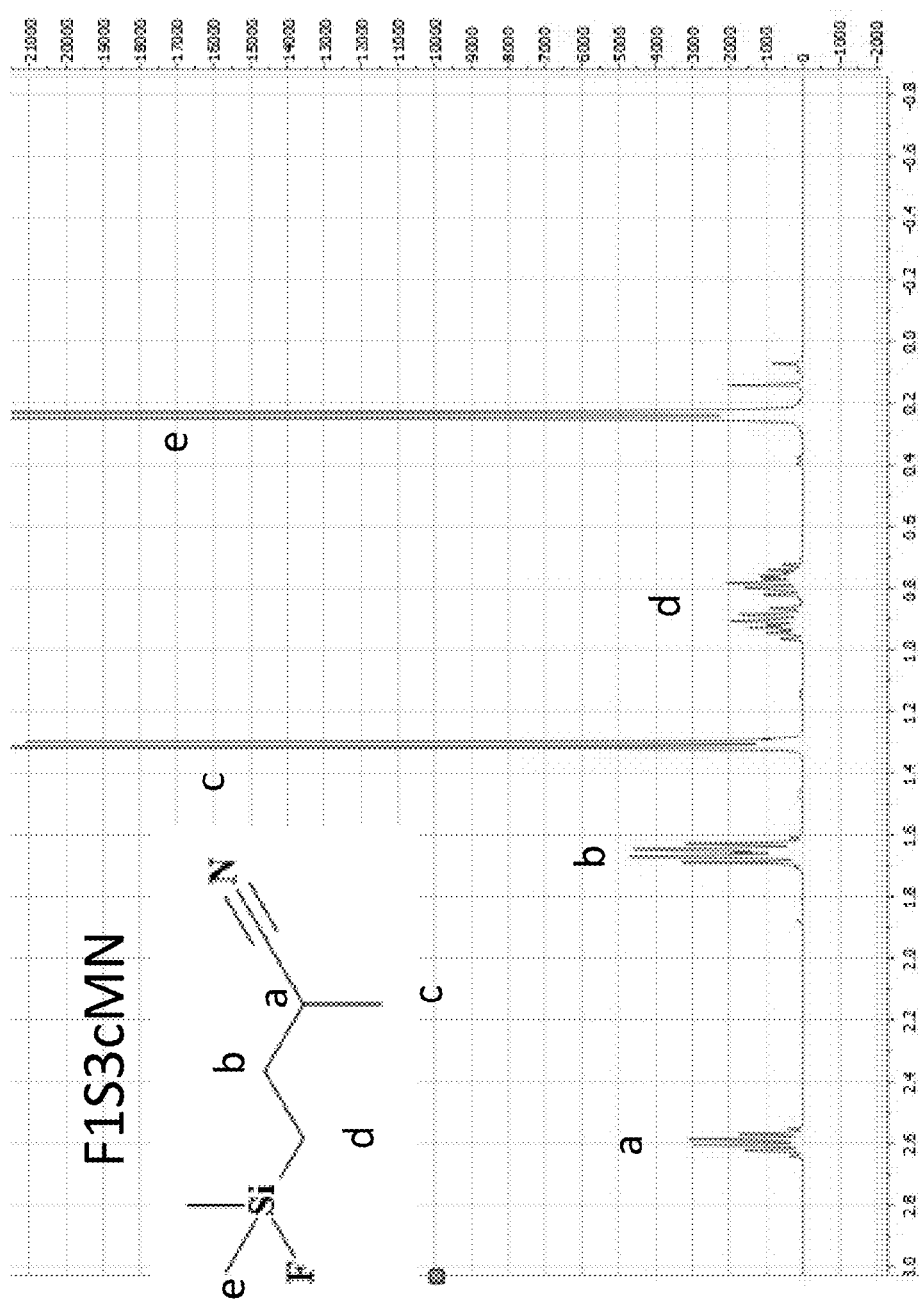
FIG. 35 is the $^1$H-NMR spectrum (in CDCl$_3$) of F1S$_3$cMN with peak assignments.
Figure 36:
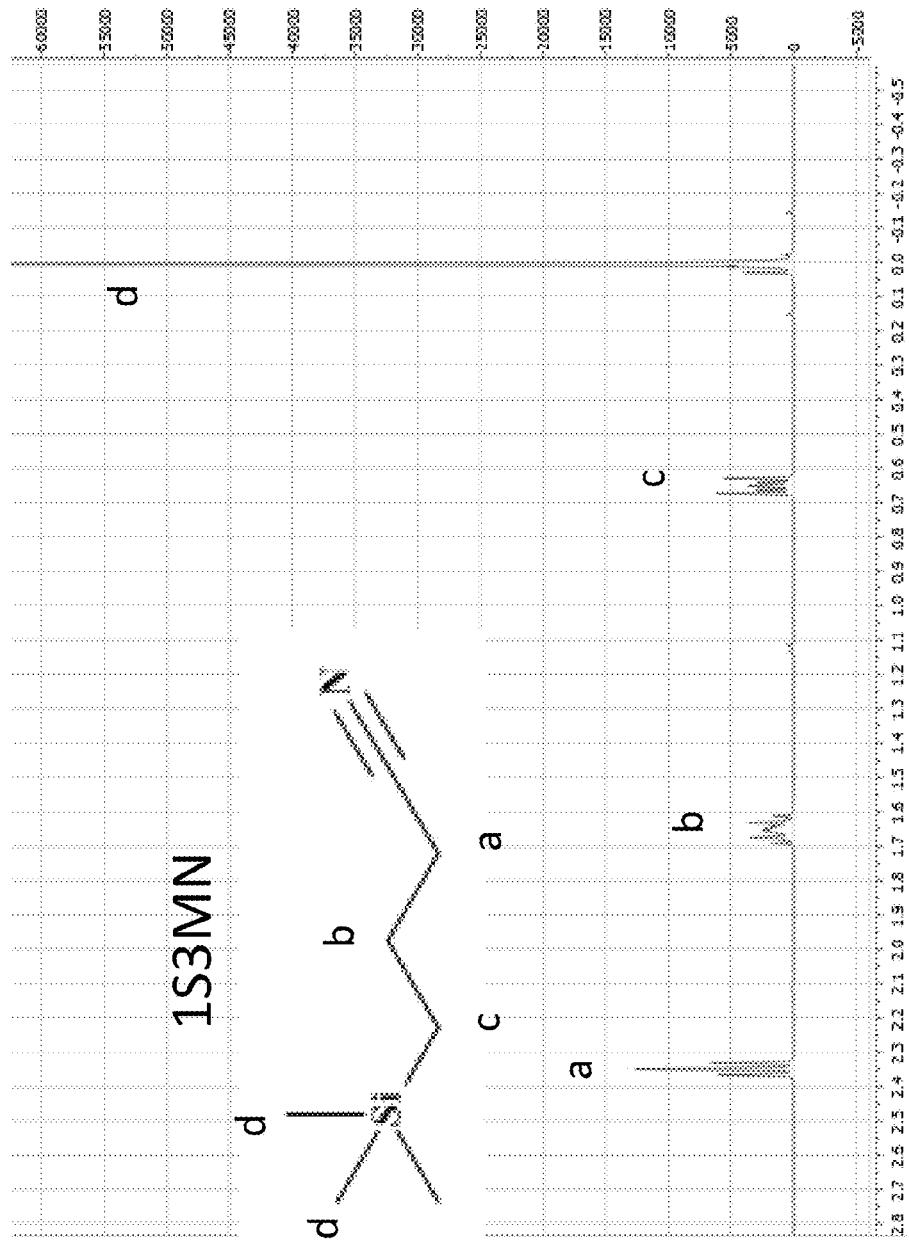
FIG. 36 is the $^1$H-NMR spectrum (in CDCl$_3$) of 1S$_3$MN with peak assignments.

FIGS. 30A and 30B depict the discharge capacity of cells containing a 1ND1N-LiPF$_6$-based electrolyte or a 1ND1N-LiTFSI-based electrolyte, respectively, at a variety of C-rates. For each experiment, a CR2032 coin cell with a Saft America (Cockeysville, Md.) NCA cathode, a graphite anode, and a 2500 separator from Celgard, LLC (Charlotte, N.C.) was used. The cells were charged with a constant-current/constant-voltage (CCCV) procedure at C/5, C/2, 1C or 2C rates to 4.1 V. The cells were discharged each cycle to 3.0 V with a constant current at the same rate that they were charged. In FIG. 30A, the 1ND1N-LiPF$_6$-based electrolyte solution included 1 M LiPF$_6$ and 1ND1N (batch ZP780-01), and the charging/discharging was performed at 30° C. or 55° C. In FIG. 30B, the 1ND1N-LiTFSI-based electrolyte solution included 1 M LiTFSI and 1ND1N, batch (ZT781-01), and the charging/discharging was performed at 30° C., 55° C., or 70° C. As shown in FIGS. 30A and 38B, the 1ND1N-LiTFSI-based electrolyte displayed better rate capability than the 1ND1N-LiPF$_6$-based electrolyte.

Physical Properties of OS Solvents and Electrolyte Solutions:

Table 1, above, shows physical properties of selected organosilicon (OS) compounds (1S$_3$MN, F1S$_3$MN, F1S$_3$cMN, DF1S$_3$MN, DF1S$_2$MN, and F1S$_3$M2) as neat solvents and formulated electrolyte solutions. Table 2, above, shows physical properties of neat 1ND1N, 1ND1, 1ND2, and F1S$_3$MN and various electrolyte compositions containing them. In both tables, the conductivity has units of mS/cm, the viscosity has units of cP, and the flash point is in degrees Celsius.

Proton ($^1$H) NMR spectra taken in CDCl$_3$ for 1ND1N, 1ND1N, DF1S$_2$MN, DF1S$_3$MN, F1S$_3$cMN, and 1S$_3$MN are presented in FIGS. 31-36, respectively. For selected compounds containing a fluorine atom, $^{19}$F-NMR data were collected in CDCl$_3$ and DMSO-d$_6$. The results are tabulated below:

| $^{19}$F-NMR in CDCl$_3$ | |
|---|---|
| F1S$_3$MN | −162.3 ppm, $^1$J($^{19}$F,$^{29}$Si) = 280 Hz |
| isoF1S$_3$MN | −166.6 ppm, $^1$J($^{19}$F,$^{29}$Si) = 284 Hz |
| DF1S$_3$MN | −135.3 ppm, $^1$J($^{19}$F,$^{29}$Si) = 296 Hz |
| TF1S$_3$MN | −136.8 ppm, $^1$J($^{19}$F,$^{29}$Si) = 280 Hz |
| DF1S$_2$MN | −135.2 ppm, $^1$J($^{19}$F,$^{29}$Si) = 296 Hz |

| $^{19}$F-NMR in DMSO-d$_6$ | |
|---|---|
| F1S$_3$MN | −159.2 ppm, $^1$J($^{19}$F,$^{29}$Si) = 279 Hz |

Conclusions:

F1S$_3$MN and 1ND1N are both suitable for use as electrolyte solvents in Li-ion batteries. F1S$_3$MN and DF1S$_2$MN have demonstrated function as electrolyte solvents in EDLC devices.

F1S$_3$MN shows very high thermal stability (measured by $^1$H NMR) with all salts tested. F1S$_3$MN shows the highest thermal stability of any OS with LiPF$_6$ (175° C.), with no observed decomposition. F1S$_3$MN does produce gas phase products as neat solvent, with LiBF$_4$, and with LiTFSI. These gas phase products can be attributed to low levels of F1S$_3$MN evaporation. F1S$_3$MN shows increased voltage stability (higher oxidation potential with wide window) compared to F1S$_3$M2. F1S$_3$MN provides equivalent performance as EPA6 up to a rate of 4C. LiBOB has limited solubility in F1S$_3$MN (<0.03M) without co-solvent, but LiBOB solubility improves (>0.1M) with use of co-solvent (i.e. 20% EC). The decomposition products of F1S$_3$MN are Me$_2$SiF$_2$ and MeSiF$_3$, both of which are gases.

1ND1N shows no gas phase decomposition as a neat solvent or in combination with LiTFSI electrolyte up to 185-190° C. The combination of 1ND1N with LiTFSI electrolyte shows promise up to 70° C. and higher. 1ND1N with LiPF$_6$ is more thermally stable than either 1ND1 or 1ND2 with LiPF$_6$. It forms acrylonitrile above 125° C. Like other non-spacer compounds, 1ND1N reacts at room temperature with LiBF$_4$. However, there is insufficient F to fully decompose the 1ND1N, and it does not form acrylonitrile. The rate performance of 1ND1N is slightly lower than 1ND2.

What is claimed is:

1. An electrolyte composition comprising a compound of Formula III,

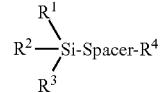

Formula III wherein R$^1$, R$^2$, and R$^3$ are the same or different and are independently selected from the group consisting of C$_1$ to C$_6$ linear or branched alkyl and fluorine, and wherein at least one of R$^1$, R$^2$, or R$^3$ is fluorine;

"Spacer" is selected from the group consisting of C$_3$ to C$_6$ linear or branched alkylene, alkenylene, or alkynylene; and R$^4$ is selected from the group consisting of cyano (—CN), cyanate (—OCN), isocyanate (—NCO), thiocyanate (—SCN) and isothiocyanate (—NCS);

in combination with a lithium-containing salt.

2. The electrolyte composition of claim 1, wherein R$^4$ is cyano.

3. The electrolyte composition of claim 1, wherein R$^1$, R$^2$, and R$^3$ are selected from the group consisting of C$_1$ to C$_3$ alkyl, and fluoro.

4. The electrolyte composition of claim 1, wherein at least two of R$^1$, R$^2$, and R$^3$ are fluorine.

5. The electrolyte composition of claim 1, wherein "Spacer" is a C3 to C$_4$ linear or branched alkylene.

6. An electrochemical device comprising an electrolyte composition as recited in claim 1.

7. The electrochemical device of claim 6, wherein R$^4$ is cyano.

8. The electrochemical device of claim 6, wherein R$^1$, R$^2$, and R$^3$ are selected from the group consisting of C$_1$ to C$_3$ alkyl, and fluoro.

9. The electrochemical device of claim 6, wherein at least two of R$^1$, R$^2$, and R$^3$ are fluorine.

10. The electrochemical device of claim 6, wherein "Spacer" is a C3 to C$_4$ linear or branched alkylene.

* * * * *